United States Patent
Sanford et al.

(10) Patent No.: US 9,861,484 B2
(45) Date of Patent: *Jan. 9, 2018

(54) ANTERIOR CRUCIATE LIGAMENT SUBSTITUTING KNEE IMPLANTS

(71) Applicant: Zimmer, Inc., Warsaw, IN (US)

(72) Inventors: Adam H. Sanford, Los Angeles, CA (US); Vincent A. Webster, Warsaw, IN (US); Dwight T Todd, Columbia City, IN (US); Anthony Romano, Columbia City, IN (US); Christopher M. Byrd, Elkhart, IN (US); Jody L. Claypool, Warsaw, IN (US); Raymond C. Parisi, Wakarusa, IN (US)

(73) Assignee: Zimmer, Inc., Warsaw, IN (US)

( * ) Notice: Subject to any disclaimer, the term of this patent is extended or adjusted under 35 U.S.C. 154(b) by 254 days.

This patent is subject to a terminal disclaimer.

(21) Appl. No.: 14/793,152

(22) Filed: Jul. 7, 2015

(65) Prior Publication Data

US 2015/0305873 A1      Oct. 29, 2015

Related U.S. Application Data

(63) Continuation of application No. 13/086,104, filed on Apr. 13, 2011, now Pat. No. 9,132,014.

(Continued)

(51) Int. Cl.
    *A61F 2/38*      (2006.01)

(52) U.S. Cl.
    CPC .............. *A61F 2/38* (2013.01); *A61F 2/389* (2013.01); *A61F 2/3859* (2013.01); *A61F 2/3886* (2013.01); *A61F 2002/3863* (2013.01)

(58) Field of Classification Search
    CPC ........ A61F 2/38; A61F 2/3836; A61F 2/3854; A61F 2/3859; A61F 2/3868; A61F 2/3886; A61F 2/389
    See application file for complete search history.

(56) References Cited

U.S. PATENT DOCUMENTS

| 3,798,679 A | 3/1974 | Ewald |
| 3,816,855 A | 6/1974 | Saleh |

(Continued)

FOREIGN PATENT DOCUMENTS

| EP | 0123016 A1 | 10/1984 |
| EP | 1121074 B1 | 7/2008 |

(Continued)

OTHER PUBLICATIONS

"U.S. Appl. No. 121692,371, Examiner Interview Summary dated Apr. 8, 2013", 3 pgs.

(Continued)

*Primary Examiner* — Marcia Watkins
(74) *Attorney, Agent, or Firm* — Schwegman Lundberg & Woessner, P.A.

(57) ABSTRACT

The present disclosure provides knee prostheses that replicate at least a portion of the function of an individual patient's anterior cruciate ligament (ACL). An exemplary knee prosthesis includes a femoral component configured to be implanted on the distal end of the patient's femur and a tibial component configured to be implanted on the proximal end of the patient's tibia. In extension, the femoral component and the tibial component may cooperate to limit anterior movement of the tibial component relative to the femoral component. In flexion, the femoral component may be free to rotate relative to the tibial component.

19 Claims, 26 Drawing Sheets

Related U.S. Application Data

(60) Provisional application No. 61/323,380, filed on Apr. 13, 2010.

(56) References Cited

U.S. PATENT DOCUMENTS

| | | |
|---|---|---|
| 4,112,522 A | 9/1978 | Dadurian et al. |
| 4,209,861 A | 7/1980 | Walker et al. |
| 4,215,439 A | 8/1980 | Gold |
| 5,147,405 A | 9/1992 | Van Zile |
| 5,219,362 A | 6/1993 | Tuke et al. |
| 5,282,870 A | 2/1994 | Moser et al. |
| 5,330,534 A | 7/1994 | Herrington et al. |
| 5,358,527 A | 10/1994 | Forte |
| 5,370,699 A | 12/1994 | Hood et al. |
| 5,413,604 A | 5/1995 | Hodge |
| 5,549,686 A | 8/1996 | Johnson et al. |
| 5,728,162 A | 3/1998 | Eckhoff |
| 6,013,103 A | 1/2000 | Kaufman et al. |
| 6,056,779 A | 5/2000 | Noyer et al. |
| 6,342,075 B1 | 1/2002 | MacArthur |
| 6,406,497 B2 | 6/2002 | Takei et al. |
| 6,475,241 B2 | 11/2002 | Pappas |
| 6,491,726 B2 | 12/2002 | Pappas |
| 6,558,426 B1 | 5/2003 | Masini |
| 6,660,039 B1 | 12/2003 | Evans et al. |
| 6,699,291 B1 | 3/2004 | Augoyard et al. |
| 6,764,516 B2 | 7/2004 | Pappas |
| 6,783,550 B2 | 8/2004 | MacArthur |
| 6,797,005 B2 | 9/2004 | Pappas |
| 7,081,137 B1 | 7/2006 | Servidio |
| 7,160,330 B2 | 1/2007 | Axelson, Jr. et al. |
| 7,309,362 B2 | 12/2007 | Yasuda et al. |
| 7,326,252 B2 | 2/2008 | Otto et al. |
| 7,351,263 B2 | 4/2008 | Afriat |
| 7,413,577 B1 | 8/2008 | Servidio |
| 7,615,054 B1 | 11/2009 | Bonutti |
| 7,635,390 B1 | 12/2009 | Bonutti |
| 8,192,498 B2 | 6/2012 | Wagner et al. |
| 8,236,061 B2 | 8/2012 | Heldreth et al. |
| 8,491,661 B2 | 7/2013 | Mouillet et al. |
| 8,932,365 B2 | 1/2015 | Parisi et al. |
| 9,132,014 B2 | 9/2015 | Sanford et al. |
| 9,615,929 B2 | 4/2017 | Sanford |
| 9,662,217 B2 | 5/2017 | Heggendorn et al. |
| 2003/0009232 A1 | 1/2003 | Metzger et al. |
| 2004/0143339 A1 | 7/2004 | Axelson, Jr. et al. |
| 2005/0209701 A1 | 9/2005 | Suguro et al. |
| 2007/0135925 A1 | 6/2007 | Walker |
| 2007/0135926 A1 | 6/2007 | Walker |
| 2007/0173946 A1 | 7/2007 | Bonutti |
| 2007/0233269 A1 | 10/2007 | Steines et al. |
| 2008/0097615 A1 | 4/2008 | Lipman et al. |
| 2008/0119940 A1 | 5/2008 | Otto et al. |
| 2009/0204221 A1* | 8/2009 | Walker ............... A61F 2/3886 623/20.27 |
| 2009/0210066 A1 | 8/2009 | Jasty |
| 2009/0222103 A1 | 9/2009 | Fitz et al. |
| 2009/0306786 A1 | 12/2009 | Samuelson |
| 2009/0319047 A1 | 12/2009 | Walker |
| 2009/0319049 A1 | 12/2009 | Shah et al. |
| 2009/0326665 A1 | 12/2009 | Wyss et al. |
| 2010/0016977 A1 | 1/2010 | Masini |
| 2010/0016979 A1 | 1/2010 | Wyss et al. |
| 2010/0036499 A1 | 2/2010 | Pinskerova |
| 2010/0042224 A1 | 2/2010 | Otto et al. |
| 2010/0161067 A1 | 6/2010 | Saleh et al. |
| 2010/0249940 A1 | 9/2010 | Sanford |
| 2010/0305708 A1 | 12/2010 | Lang |
| 2010/0329530 A1 | 12/2010 | Lang et al. |
| 2011/0144760 A1 | 6/2011 | Wong et al. |
| 2012/0089234 A1 | 4/2012 | Mouillet et al. |
| 2012/0095563 A1 | 4/2012 | Sanford et al. |
| 2012/0095564 A1 | 4/2012 | Mihalko et al. |
| 2012/0179265 A1 | 7/2012 | Wyss et al. |
| 2012/0323337 A1 | 12/2012 | Parisi et al. |
| 2013/0006373 A1 | 1/2013 | Wyss et al. |
| 2013/0190884 A1 | 7/2013 | Hashida |
| 2013/0197653 A1 | 8/2013 | Hawkins et al. |
| 2013/0204380 A1 | 8/2013 | Mouillet et al. |
| 2014/0243989 A1 | 8/2014 | Nabeshima et al. |
| 2015/0025644 A1 | 1/2015 | Heggendorn et al. |
| 2015/0134067 A1 | 5/2015 | Qu et al. |
| 2015/0164646 A1 | 6/2015 | Muratoglu |
| 2017/0165079 A1 | 6/2017 | Sanford |

FOREIGN PATENT DOCUMENTS

| | | |
|---|---|---|
| EP | 1555962 B1 | 2/2011 |
| EP | 2324799 A2 | 5/2011 |
| EP | 2335654 A1 | 6/2011 |
| JP | 2004166802 A | 6/2004 |
| WO | WO-0023011 A1 | 4/2000 |
| WO | WO-2005051240 A1 | 6/2005 |
| WO | WO-2006058057 A2 | 6/2006 |
| WO | WO-2007109641 A2 | 9/2007 |
| WO | WO-2011018441 A1 | 2/2011 |
| WO | WO-2011072235 A2 | 6/2011 |
| WO | WO-2012031774 A1 | 3/2012 |
| WO | WO-2012112698 A2 | 8/2012 |
| WO | WO-2013007747 A1 | 1/2013 |

OTHER PUBLICATIONS

"U.S. Appl. No. 12/692,371, Final Office Action dated Sep. 25, 2013", 9 pgs.

"U.S. Appl. No. 12/692,371, Non Final Office Action dated Apr. 9, 2015", 8 pgs.

"U.S. Appl. No. 12/692,371, Non Final Office Action dated Oct. 26, 2011", 8 pgs.

"U.S. Appl. No. 12/692,371, Response filed Jan. 26, 2012 to Non Final Office Action dated Oct. 26, 2011", 12 pgs.

"U.S. Appl. No. 12/692,371, Response filed Feb. 25, 2014 to Final Office Action dated Sep. 25, 2013", 15 pgs.

"U.S. Appl. No. 12/692,371, Response filed May 11, 2012 to Non Final Office Action dated Oct. 26, 2011", 3 pgs.

"U.S. Appl. No. 12/692,371, Response filed Aug. 26, 2011 to Restriction Requirement dated Jul. 7, 2011", 2 pgs.

"U.S. Appl. No. 12/692,371, Restriction Requirement dated Jul. 7, 2011", 6 pgs.

"U.S. Appl. No. 13/086,104, Advisory Action dated Apr. 1, 2015", 3 pgs.

"U.S. Appl. No. 13/086,104, Final Office Action dated Jan. 27, 2015", 12 pgs.

"U.S. Appl. No. 13/086,104, Final Office Action dated Apr. 9, 2013", 8 pgs.

"U.S. Appl. No. 13/086,104, Non Final Office Action dated May 28, 2014", 15 pgs.

"U.S. Appl. No. 13/086,104, Non Final Office Action dated Oct. 18, 2012", 12 pgs.

"U.S. Appl. No. 13/086,104, Notice of Allowance dated May 1, 2015", 5 pgs.

"U.S. Appl. No. 13/086,104, Response filed Feb. 19, 2013 to Non Final Office Action dated Oct. 18, 2012", 16 pgs.

"U.S. Appl. No. 13/086,104, Response filed Mar. 26, 2015 to Final Office Action dated Jan. 27 2015", 16 pgs.

"U.S. Appl. No. 13/086,104, Response filed Apr. 21, 2015 to Advisory Action dated Apr. 1, 2015", 16 pgs.

"U.S. Appl. No. 13/086,104, Response filed Jul. 9, 2013 to Final Office Action mailed Apr. 9, 2013", 13 pgs.

"U.S. Appl. No. 13/086,104, Response filed Oct. 1, 2012 to Restriction Requirement dated Aug. 29, 2012", 6 pgs.

"U.S. Appl. No. 13/086,104, Response filed Nov. 24, 2014 to Non Final Office Action dated May 28, 2014", 15 pgs.

"U.S. Appl. No. 13/086,104, Restriction Requirement dated Aug. 29, 2012", 6 pgs.

"U.S. Appl. No. 14/131,986, Preliminary Amendment filed Jan. 10, 2014", 3 pgs.

(56) References Cited

OTHER PUBLICATIONS

"U.S. Appl. No. 14/509,753, Preliminary Amendment filed Oct. 8, 2014", 3 pgs.
"Complete Knee Solution Surgical Technique for the CR-Flex Fixed Bearing Knee", Zimmer Nexgen, (2003), 22 pgs.
"International Application Serial No. PCT/EP2012/063575, Demand and Letter filed May 13, 2013", 11 pgs.
"International Application Serial No. PCT/EP2012/063575, International Preliminary Report on Patentability dated Dec. 2, 2013", 9 pgs.
"International Application Serial No. PCT/EP2012/063575, International Search Report dated Oct. 11, 2012", 5 pgs.
"International Application Serial No. PCT/EP2012/063575, Written Opinion dated Oct. 11, 2012", 7 pgs.
"International Application Serial No. PCT/US2010/021818, International Preliminary Report on Patentability dated Jul. 26, 2011", 8 pgs.
"International Application Serial No. PCT/US2010/021818, International Search Report dated Apr. 20, 2010", 4 pgs.
"International Application Serial No. PCT/US2010/021818, Written Opinion dated Apr. 20, 2010", 8 pgs.
"LPS Flex Fixed Bearing Knee", Zimmer Surgical Technique, (2004, 2007), 12 pgs.
"U.S. Appl. No. 12/692,371, Non Final Office Action dated May 18, 2016", 13 pgs.
"U.S. Appl. No. 12/692,371, Response filed Jan. 20, 2016 to Non-Final Office Action dated Oct. 20, 2015", 16 pgs.
"U.S. Appl. No. 12/692,371, Response filed Jun. 16, 2015 to Non-Final Office Action dated Apr. 9, 2015", 17 pgs.
"U.S. Appl. No. 12/692,371, Response filed Aug. 18, 2016 to Non Final Office Action dated May 18, 2016", 15 pgs.
"U.S. Appl. No. 14/509,753, Final Office Action dated Jul. 7, 2016", 5 pgs.
"U.S. Appl. No. 14/509,753, Non Final Office Action dated Jan. 25, 2016", 9 pgs.
"U.S. Appl. No. 14/509,753, Response filed May 4, 2016 to Non Final Office Action dated Jan. 25, 2016", 14 pgs.
"U.S. Appl. No. 14/826,807, Non Final Office Action dated Oct. 20, 2015" 9 pgs.
"U.S. Appl. No. 61/381,803, Application filed Sep. 10, 2010", 23 pgs.
"U.S. Appl. No. 14/509,753, Response filed Sep. 7, 2016 to Final Office Action dated Jul. 7, 2016", 9 pgs.
"U.S. Appl. No. 12/692,371, Notice of Allowance dated Dec. 5, 2016", 7 pgs.
"U.S. Appl. No. 14/509,753, Notice of Allowance dated Feb. 8, 2017", 7 pgs.
"U.S. Appl. No. 14/509,753, Notice of Allowance dated Sep. 19, 2016", 8 pgs.
"U.S. Appl. No. 15/442,925, Preliminary Amendment filed Mar. 3, 2017", 8 pgs.
"U.S. Appl. No. 15/442,925, Restriction Requirement dated Jul. 5, 2017", 6 pgs.
"Bi-Cruciate Stabilized Knee System", Design Rationale, Smith & Nephew Journal, (2006), 20 pgs.
Li, Guoan, et al., "Anterior Cruciate Ligament Deficiency Alters the In Vivo Motion of the Tibiofemoral Cartilage Contact Points in Both the Anteroposterior and Mediolateral Directions", The Journal of Bone & Joint Surgery, (2006), 1826-1834.

* cited by examiner

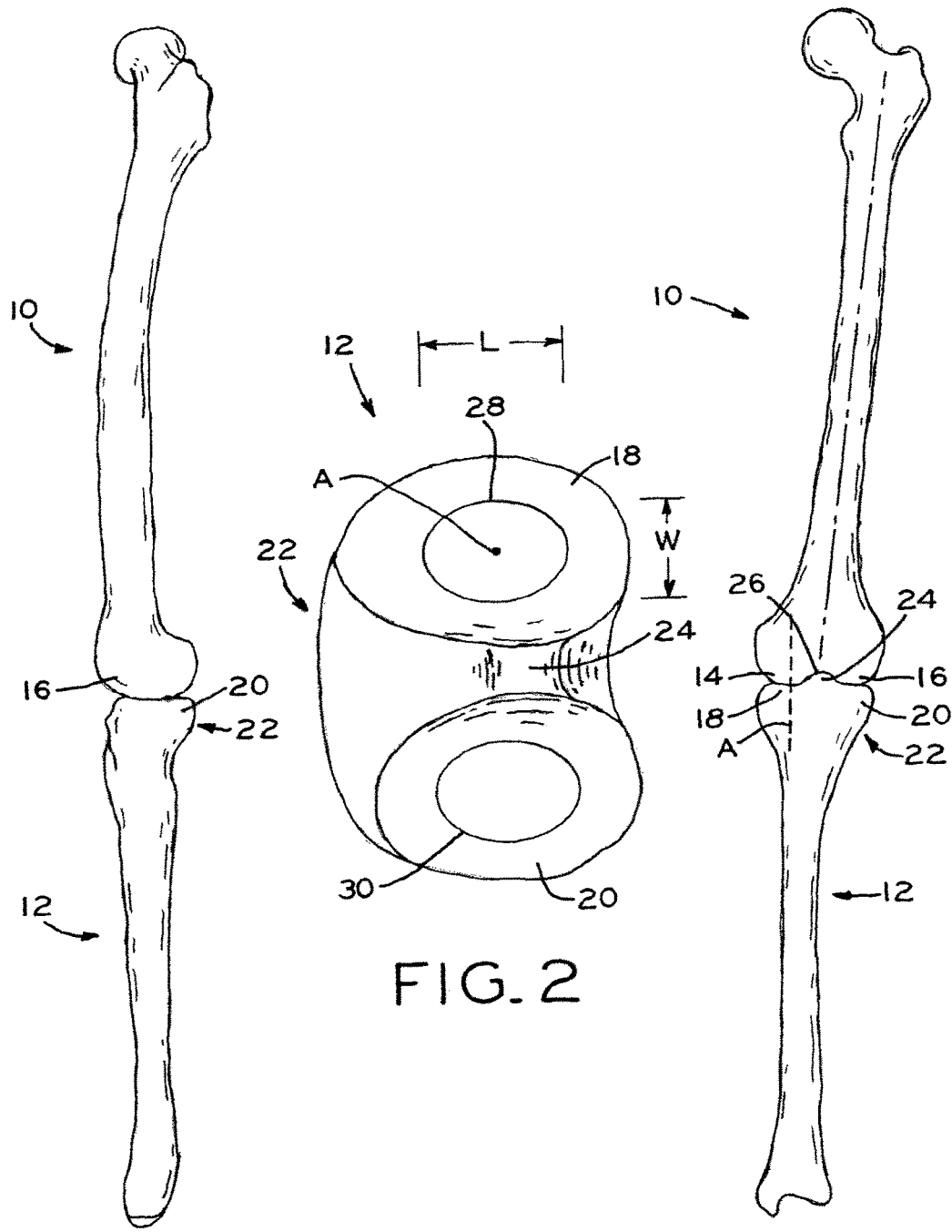

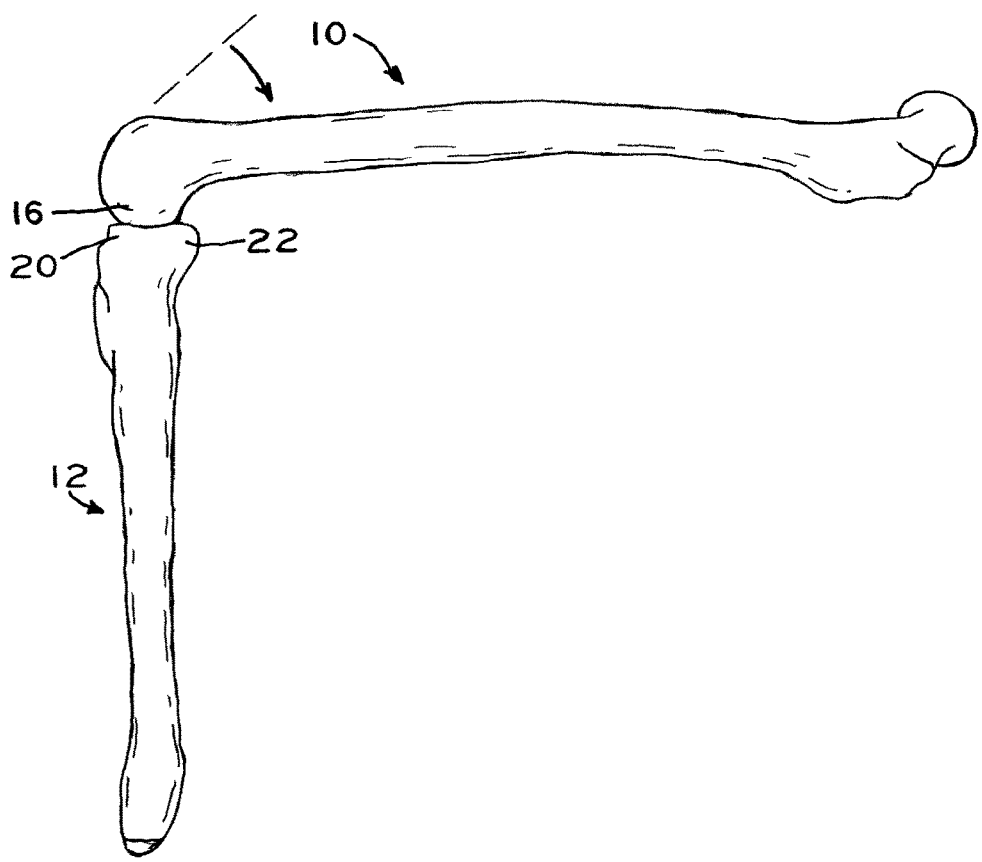
FIG_6
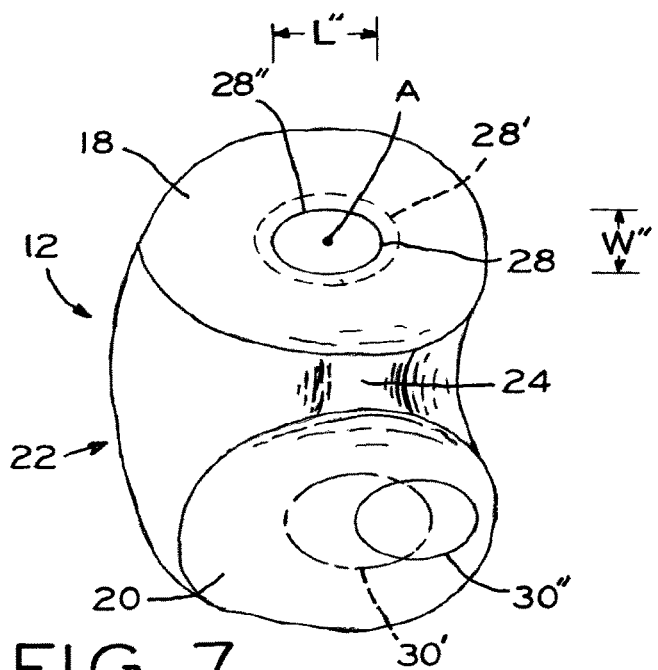
FIG_7

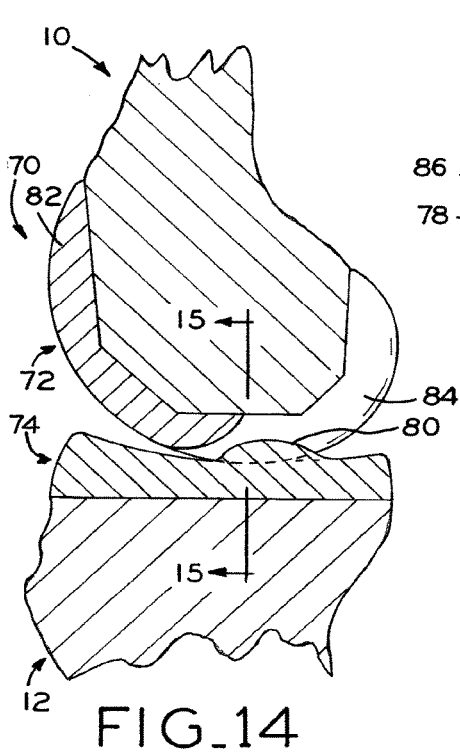
FIG_14
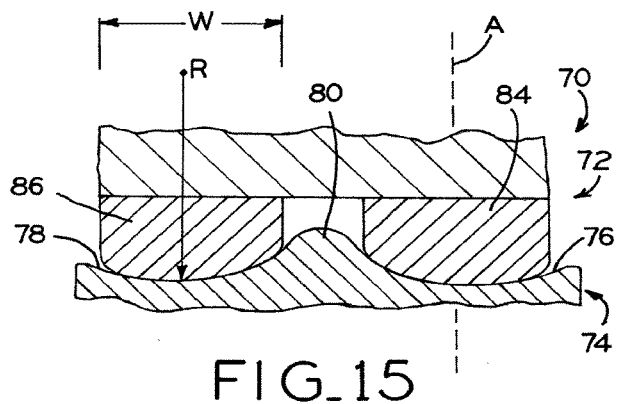
FIG_15
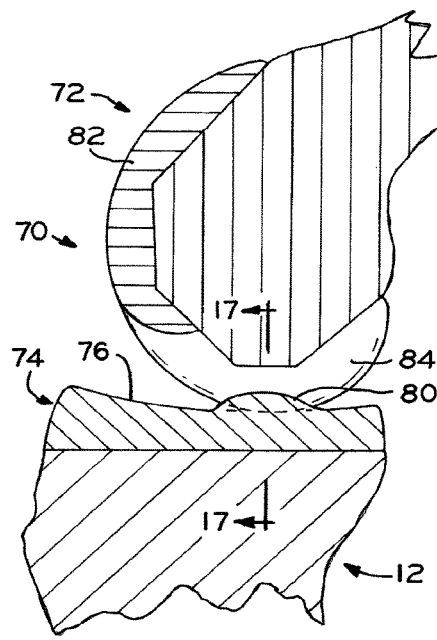
FIG_16
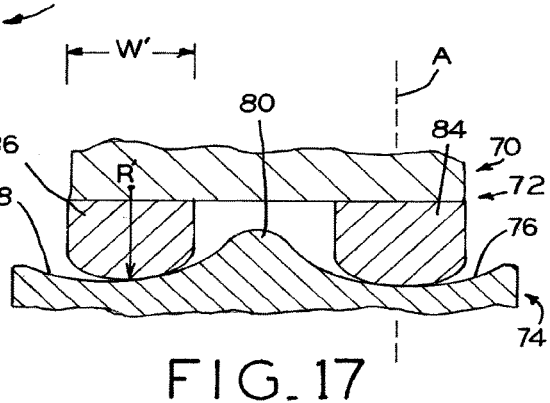
FIG_17

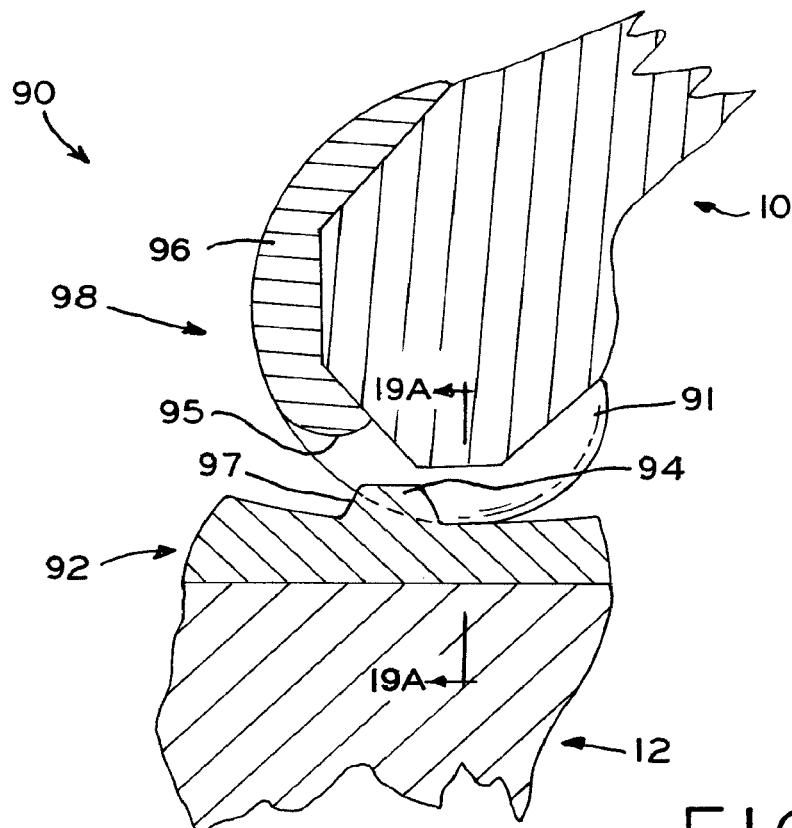
FIG_19
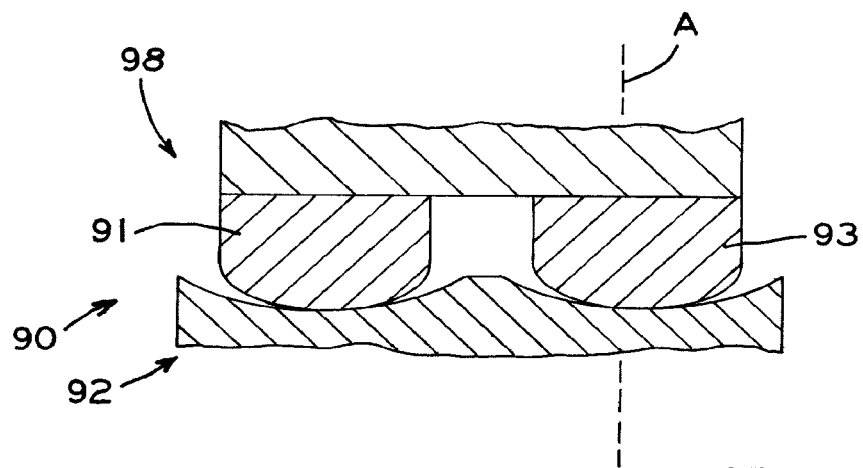
FIG_19A

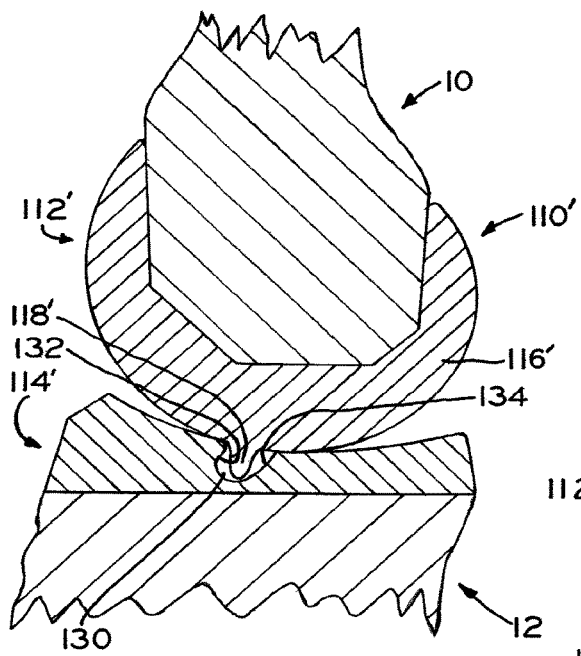
FIG_22
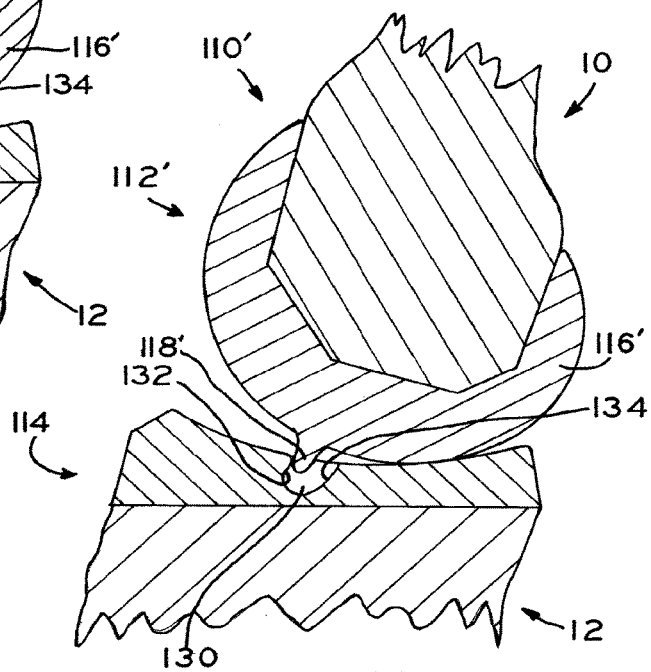
FIG_23
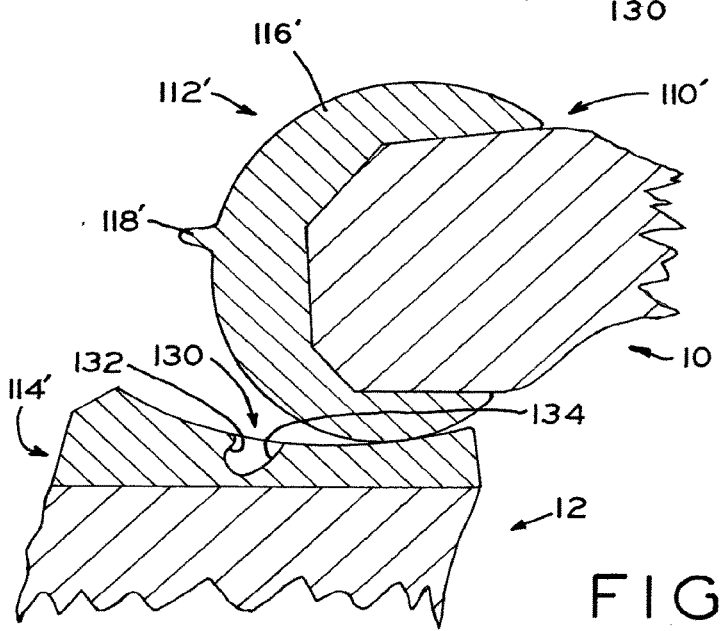
FIG_24

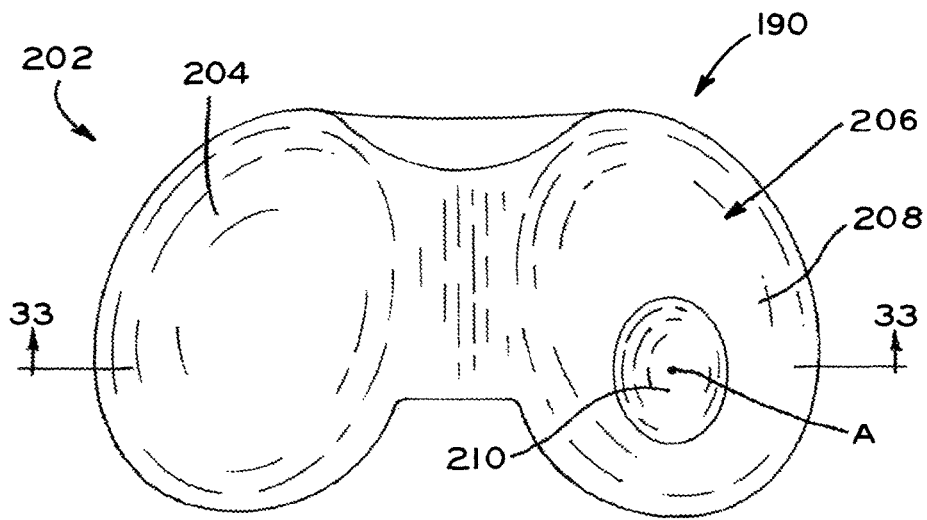
FIG_32
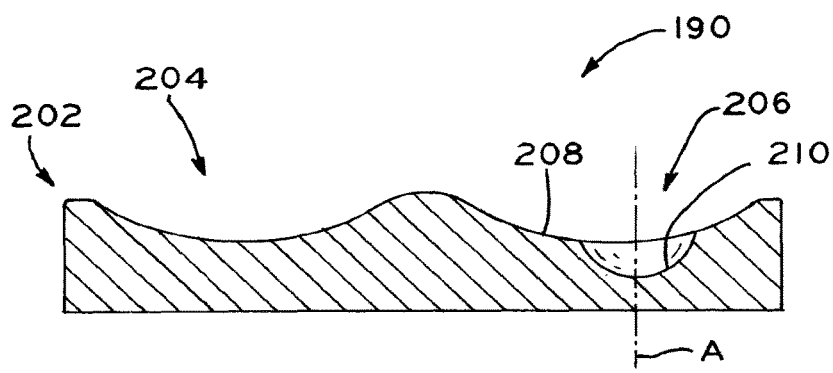
FIG_33

FIG_51

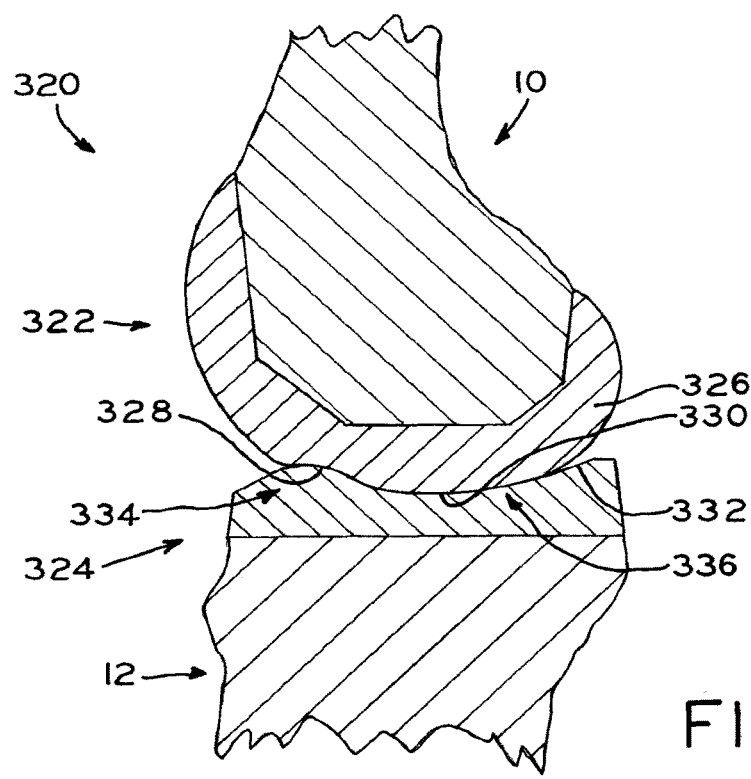
FIG_54
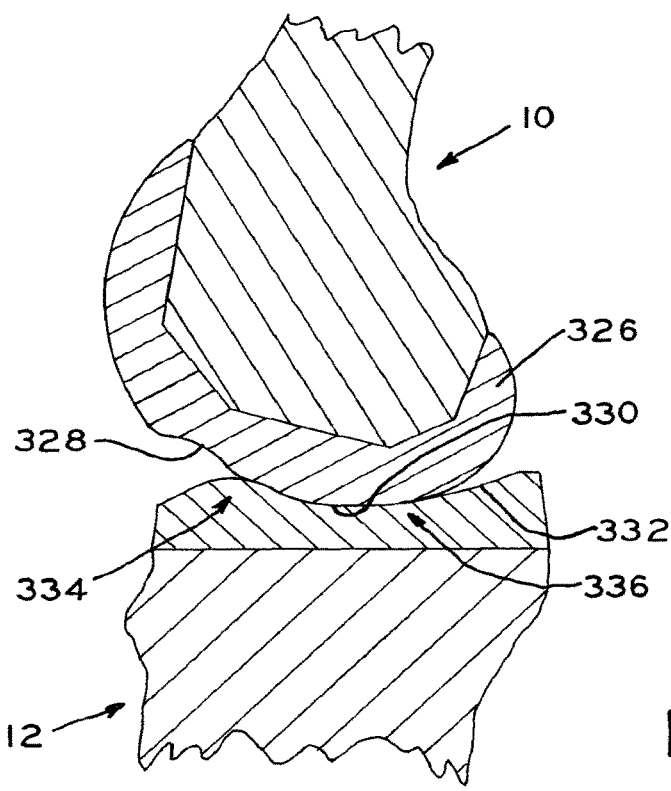
FIG_55

ANTERIOR CRUCIATE LIGAMENT SUBSTITUTING KNEE IMPLANTS

CROSS REFERENCE TO RELATED APPLICATION

This application is a continuation of U.S. patent application Ser. No. 13/086,104, filed on 13 Apr. 2011, now U.S. Pat. No. 9,132,014, which application claims priority from U.S. Provisional Patent Application Ser. No. 61/323,380, entitled "Anterior Cruciate Substituting Knee Implants," filed Apr. 13, 2010, the disclosures of which are hereby expressly incorporated by reference herein in their entirety.

FIELD OF THE DISCLOSURE

The present disclosure relates to prosthetic implants and, specifically, to anterior cruciate ligament substituting knee implants.

BACKGROUND OF THE DISCLOSURE

In a natural knee joint, the distal end of the femur articulates against the proximal end of the tibia. The knee joint is supported by various ligaments, including the posterior cruciate ligament (PCL) and the anterior cruciate ligament (ACL). These ligaments stabilize the knee joint while at rest in full extension. Also, these ligaments cooperate to control the complex movements of the knee joint during flexion and extension. The PCL originates medially on the distal femur and attaches to the posterior side of the proximal tibia to resist posterior translation of the tibia relative to the femur. The ACL, on the other hand, originates at the distal femur and attaches to the anterior side of the proximal tibia to resist anterior translation of the tibia relative to the femur.

During flexion and extension of the knee joint, the ligaments of the knee joint work in concert with the meniscus and the geometry of the femur and tibia to effect rotation of the femur about an axis that is offset in a medial direction relative to the center of the knee joint. As a result, the lateral femoral condyle travels along an arcuate path across the proximal tibia, while the medial femoral condyle maintains a relatively central position on the proximal tibia.

Referring to FIGS. 1-7, a natural knee joint is shown in various degrees of flexion and extension.

The knee joint is shown in full extension in FIGS. 1-3. When the knee joint is in extension, femur 10 and tibia 12 are aligned such that, from the side view of FIG. 1, femur 10 and tibia 12 extend along a substantially straight line. In this position, medial and lateral condyles 14, 16, of femur 10 are positioned atop medial and lateral portions 18, 20, of tibial plateau 22, respectively. Ovals 28, 30, of FIG. 2 depict the contact area of medial and lateral femoral condyles 14, 16, respectively, upon tibial plateau 22. As shown, contact areas 28, 30, of medial and lateral femoral condyles 14, 16, are generally centered atop tibial plateau 22. Contact areas 28, 30, of medial and lateral femoral condyles 14, 16, have sufficient length L and width W to provide stability to the knee joint when in extension. Additionally, as shown in FIG. 3, intercondylar eminence 24 of tibial plateau 22 extends proximally into intercondylar notch 26 of femur 10 to provide additional stability to the knee joint. In this position, the ACL (not shown) resists anterior translation of the tibia 12 relative to the femur 10.

The knee joint is shown in mid-flexion in FIGS. 4 and 5. Specifically, the knee joint is bent such that femur 10 is rotated relative to tibia 12 by approximately 45°. As the knee joint moves into mid-flexion, the femur 10 rotates about an axis A that is medially offset from a centerline of the knee joint. Therefore, contact area 30' of lateral femoral condyle 16 advances posteriorly from full extension to mid-flexion, as shown in FIG. 5 by comparing the contact area 30 in full extension (shown in phantom) with the contact area 30' in mid-flexion (shown in solid lines). Also, contact area 30' of lateral femoral condyle 16 advances posteriorly relative to contact area 28' of medial femoral condyle 14. Additionally, as the knee joint moves into mid-flexion, contact areas 28', 30', decrease in length L' and width W', because the radius of curvature of medial and lateral femoral condyles 14, 16, decreases posteriorly both in a plane parallel to a sagittal plane (e.g., along length L) and in a coronal plane (e.g., along width W).

The knee joint is shown in a state of increased flexion in FIGS. 6 and 7. Specifically, the knee joint is bent such that femur 10 is rotated relative to tibia 12 by another 45°, with femur 10 and tibia 12 forming an angle of approximately 90° therebetween. As the knee joint continues to bend, the femur 10 continues to rotate about axis A. Therefore, contact area 30" of lateral femoral condyle 16 advances posteriorly from mid-flexion to full flexion, as shown in FIG. 7 by comparing the contact area 30' in mid-flexion (shown in phantom) with the contact area 30" in full flexion (shown in solid lines). Additionally, as the knee joint continues to bend, contact areas 28 ", 30 ", decrease further in length L" and width W". The reduced size of contact areas 28 ", 30 ", eases the ability for femur 10 to rotate relative to tibia 12 about axis A.

Because the lateral femoral condyle 16 travels further across tibial plateau 22 than medial femoral condyle 14, tibia 12 rotates relative to femur 10 during flexion and extension. As the knee joint flexes from full extension (FIG. 2) to mid-extension (FIG. 5), tibia 12 rotates internally relative to femur 10. Conversely, as the knee joint extends from mid-extension (FIG. 5) to full extension (FIG. 2), tibia 12 rotates externally relative to femur 10. This external rotation of tibia 12 tightens the ligaments of the knee joint and "locks" the knee joint against further rotation to stabilize the knee joint in full extension. This behavior of the knee joint when reaching full extension is known as the "screw home mechanism."

When a normal knee joint becomes damaged and knee arthroplasty is required, it may be necessary to sacrifice ligaments of the knee joint, including the ACL. However, without the ACL, it may be difficult to recreate the stability and the complex movements of the natural knee joint. For example, without the ACL, the tibia may translate anteriorly relative to the femur. Also, without the ACL, the lateral femoral condyle may not rotate about a medially offset axis.

SUMMARY OF THE DISCLOSURE

The present disclosure provides knee prostheses that replicate at least a portion of the function of an individual patient's anterior cruciate ligament (ACL). The knee prostheses of the present disclosure may also accommodate a healthy, functional posterior cruciate ligament (PCL). An exemplary knee prosthesis includes a femoral component configured to be implanted on the distal end of the patient's femur and a tibial component configured to be implanted on the proximal end of the patient's tibia. In extension, the femoral component and the tibial component may cooperate to limit anterior movement of the tibial component relative to the femoral component. In flexion, the femoral component may be free to translate and/or rotate relative to the tibial component.

According to an exemplary embodiment of the present disclosure, a knee prosthesis is provided that articulates between a substantially extended position and a flexed position. The knee prosthesis includes an axis that is medially offset from a center of the knee prosthesis. The knee prosthesis further includes a femoral component including a medial condyle and a lateral condyle and a tibial component including a medial surface sized to receive the medial condyle of the femoral component and a lateral surface sized to receive the lateral condyle of the femoral component. The femoral and tibial components are more constrained against at least one of the following movements when the knee prosthesis is in the substantially extended position than when the knee prosthesis is in the flexed position: a rotational movement of the femoral component relative to the tibial component about the axis; an anterior movement of the tibial component relative to the femoral component; and a lateral movement of the femoral component relative to the tibial component, whereby the knee prosthesis resists at least one of the rotational movement and the anterior movement to a greater extent when the knee prosthesis is in the substantially extended position than when the knee prosthesis is in the flexed position.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is a lateral, elevational view of a left knee joint in full extension, the knee joint formed between a femur and a tibia;

FIG. 2 is a plan view of the tibia of FIG. 1 depicting the area of contact between the tibia and the femur in full extension;

FIG. 3 is an anterior, elevational view of the knee joint of FIG. 1;

FIG. 6 is a lateral, elevational view of the knee joint of FIG. 1 in a state of further flexion;

FIG. 7 is a plan view of the tibia of FIG. 6 depicting the area of contact between the tibia and the femur in the state of further flexion;

FIG. 14 is a cross-sectional view of another exemplary knee prosthesis in full extension;

FIG. 15 is a partial, cross-sectional view of the knee prosthesis of FIG. 14, taken along line 15-15 of FIG. 14;

FIG. 16 is a view similar to FIG. 14 showing the knee prosthesis in early flexion;

FIG. 17 is a partial, cross-sectional view of the knee prosthesis of FIG. 16, taken along line 17-17 of FIG. 16;

FIG. 19 is a view similar to FIG. 18 showing the knee prosthesis in early flexion;

FIG. 19A is a partial, cross-sectional view of the knee prosthesis of FIG. 19, taken along line 19A-19A of FIG. 19;

FIG. 22 is a cross-sectional view of yet another exemplary knee prosthesis in full extension;

FIG. 23 is a view similar to FIG. 22 showing the knee prosthesis in early flexion;

FIG. 24 is a view similar to FIG. 23 showing the knee prosthesis in a state of further flexion;

FIG. 32 is a plan view of a tibial component of yet another exemplary knee prosthesis;

FIG. 33 is a cross-sectional view of the tibial component of FIG. 32, taken along line 33-33 of FIG. 32;

FIG. 54 is a medial cross-sectional view of still yet another exemplary knee prosthesis in full extension;

FIG. 55 is a view similar to FIG. 54 showing the knee prosthesis in early flexion;

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figures 4, 5:
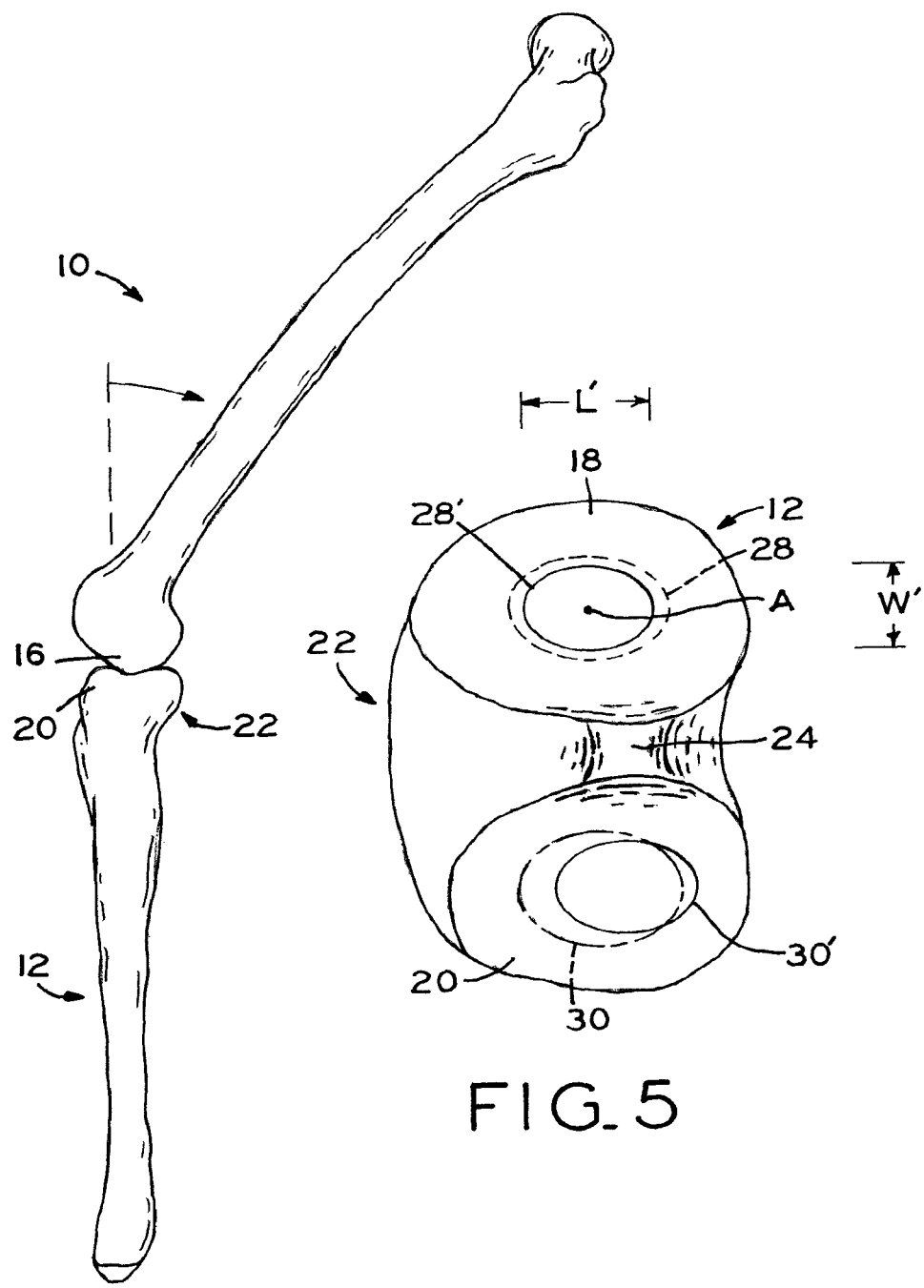
FIG. 4 is a lateral, elevational view of the knee joint of FIG. 1 in early flexion.
FIG. 5 is a plan view of the tibia of FIG. 4 depicting the area of contact between the tibia and the femur in early flexion.

As discussed above with respect to FIGS. 1-7, the natural knee joint is supported by various ligaments, including the posterior cruciate ligament (PCL) and the anterior cruciate ligament (ACL). These ligaments work in concert with the meniscus and the geometry of the femur and tibia to effect rotation of femur 10 about a medially offset axis A relative to tibia 12. Also, the ACL, in particular, resists anterior translation of tibia 12 relative to the femur 10.

In certain cases, the ACL must be sacrificed. The knee joint prostheses of the present disclosure function to replicate at least one of the beneficial aspects of the ACL. When the knee joint is located in full extension or somewhere between full extension and early flexion (also referred to herein as "substantially extended positions"), the knee joint prostheses of the present disclosure may be arranged in a first configuration that is more restricted to movement. For example, the knee joint prostheses of the present disclosure may resist anterior translation of tibia 12 relative to the femur 10 in the first configuration. As another example, the knee joint prostheses of the present disclosure may limit rotation of tibia 12 relative to femur 10 in the first configuration. However, when the knee joint flexes beyond early flexion, the knee joint prostheses of the present disclosure may be arranged in a second configuration that is less restricted to movement.

The point at which the knee joint prosthesis transitions from the first, more restricted configuration to the second, less restricted configuration may vary depending on the needs of particular patients. For example, in certain embodiments, the knee joint prosthesis may enter the second, less restricted configuration at approximately 10°, 20°, or 30° of knee flexion (i.e., early flexion), such that the knee joint prosthesis is arranged in the first, more restricted configuration in the substantially extended positions of 0° of knee flexion (i.e., full extension) up to approximately 10°, 20°, or 30° of knee flexion (i.e., early flexion). It is within the scope of the present disclosure that the transition from the first configuration to the second configuration may occur gradually, such as over 5°, 10°, or more, of knee flexion.

Referring to FIGS. 8-13, an exemplary knee prosthesis 40 is shown. Knee prosthesis 40 includes femoral component 42 and tibial component 44. Femoral component 42 and tibial component 44 are implanted onto femur 10 and tibia 12, respectively, in a known manner.

Figure 8:
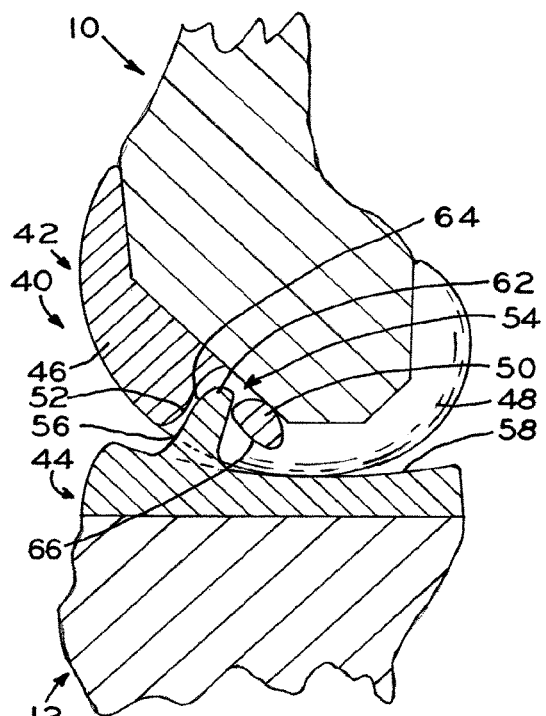
FIG. 8 is a cross-sectional view of an exemplary knee prosthesis in full extension, the knee prosthesis including a femoral component and a tibial component.

Femoral component 42 of knee prosthesis 40 includes an anterior patello-femoral flange 46, medial condyle 48, and an opposing lateral condyle (not shown). Optionally, femoral component 42 may also include crossbar 50. Crossbar 50 extends between medial condyle 48 and the opposing lateral condyle of femoral component 42. Crossbar 50 is spaced apart from the distal-most end 52 of patello-femoral flange 46 and cooperates with patello-femoral flange 46 to define opening 54 therebetween. As shown in FIG. 8, opening 54 is sized for receipt of projection 56 therein, which extends proximally from tibial component 44. In one exemplary embodiment, the distal-most end 52 of patello-femoral flange 46 and/or distal wall 66 of crossbar 50 are slanted distally in an anterior-posterior direction to define a funnel-shaped opening 54 therebetween.

Figure 9:
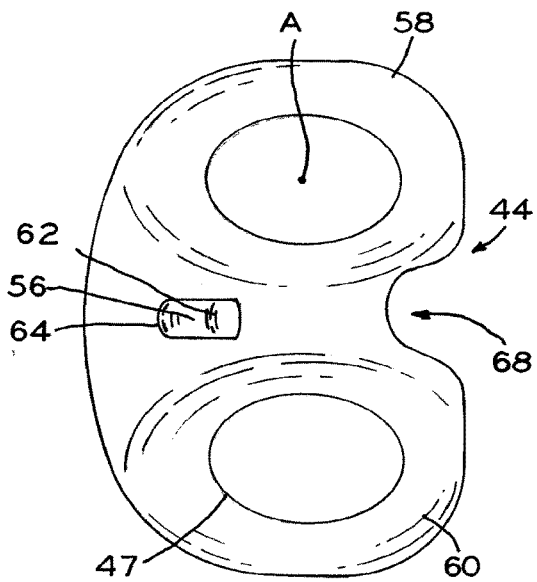
FIG. 9 is a plan view of the tibial component of FIG. 8 depicting the area of contact between the tibial component and the femoral component in full extension.

Tibial component 44 of knee prosthesis 40 is shown in FIG. 9. Tibial component 44 includes medial articulating surface 58 and lateral articulating surface 60. Medial and lateral articulating surfaces 58, 60, are formed in a traditional manner as generally concave surfaces. Projection 56 is positioned between medial and lateral articulating surfaces 58, 60, of tibial component 44 and extends proximally and slightly posteriorly from the proximal surface of tibial component 44. In one exemplary embodiment, projection 56 terminates proximally at curved end 62 and includes partially curved anterior wall 64. To accommodate the patient's PCL, tibial component 44 may include posterior cutout 68.

With the knee joint in extension, as shown in FIGS. 8 and 9, projection 56 of tibial component 44 is received within opening 54 of femoral component 42. If tibia 12 were forced anteriorly relative to femur 10 in this extended position, anterior wall 64 of projection 56 would abut the distal-most end 52 of patello-femoral flange 46 to limit anterior movement of tibia 12 relative to femur 10. Also, if tibia 12 were forced posteriorly relative to femur 10 in this extended position, projection 56 would abut crossbar 50 to limit posterior movement of tibia 12 relative to femur 10.

Figure 10:
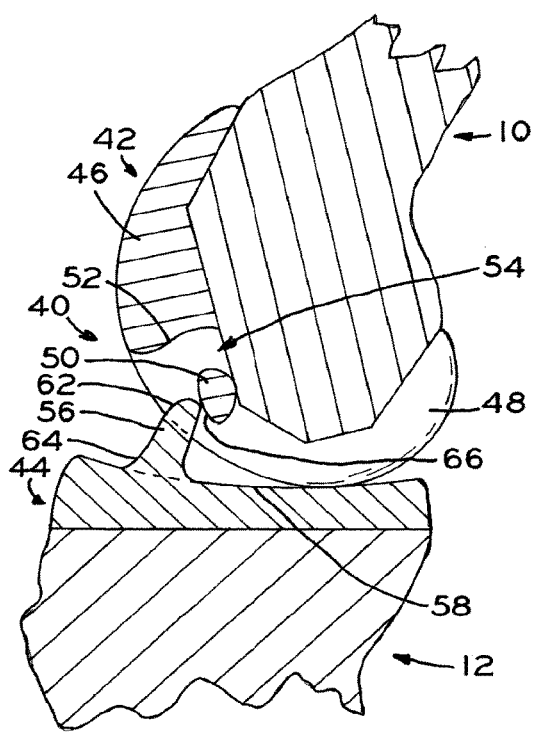
FIG. 10 is a view similar to FIG. 8 showing the knee prosthesis in early flexion.
Figure 11:
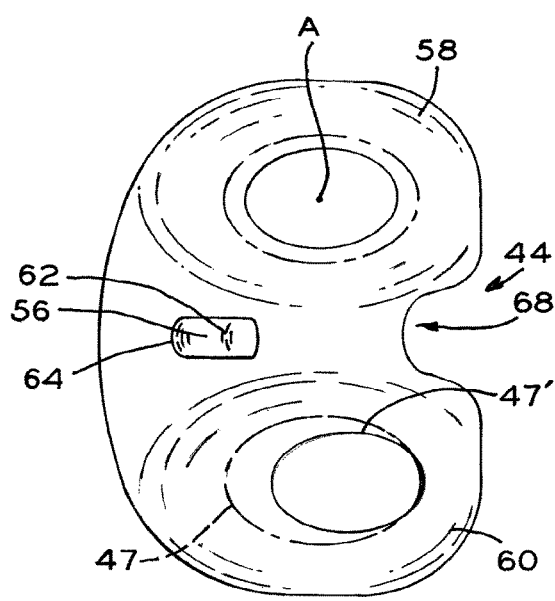
FIG. 11 is a plan view of the tibial component of FIG. 10 depicting the area of contact between the tibial component and the femoral component in early flexion.

As the knee joint reaches early flexion, as shown in FIGS. 10 and 11, the curved proximal end 62 of projection 56 may slide across the slanted, distal wall 66 of crossbar 50. By maintaining contact between projection 56 and crossbar 50 during early flexion, femur 10 is prevented from sliding anteriorly relative to tibia 12, and tibia 12 is prevented from sliding posteriorly relative to femur 10.

In an exemplary embodiment, patello-femoral flange 46, projection 56, and/or crossbar 50 may interact to drive rotation of femoral component 42 relative to tibial component 44 about a medially offset axis A. For example, the shape and/or orientation of patello-femoral flange 46, crossbar 50, and/or projection 56 may vary in a medial-lateral direction to force the lateral condyle (not shown) of femoral component 42 to rotate about axis A. As a result, during flexion of the knee joint, contact area 47' of the lateral condyle of femoral component 42 advances posteriorly from full extension to early flexion, as shown in FIG. 11 by comparing the contact area 47 in full extension (shown in phantom) with the contact area 47' in early flexion (shown in solid lines). By modifying the shape and/or orientation of patello-femoral flange 46, crossbar 50, and/or projection 56, the rotation and posterior movement of femoral component 42 and tibial component 44 relative to one another can be correspondingly modified.

Figures 12, 13:
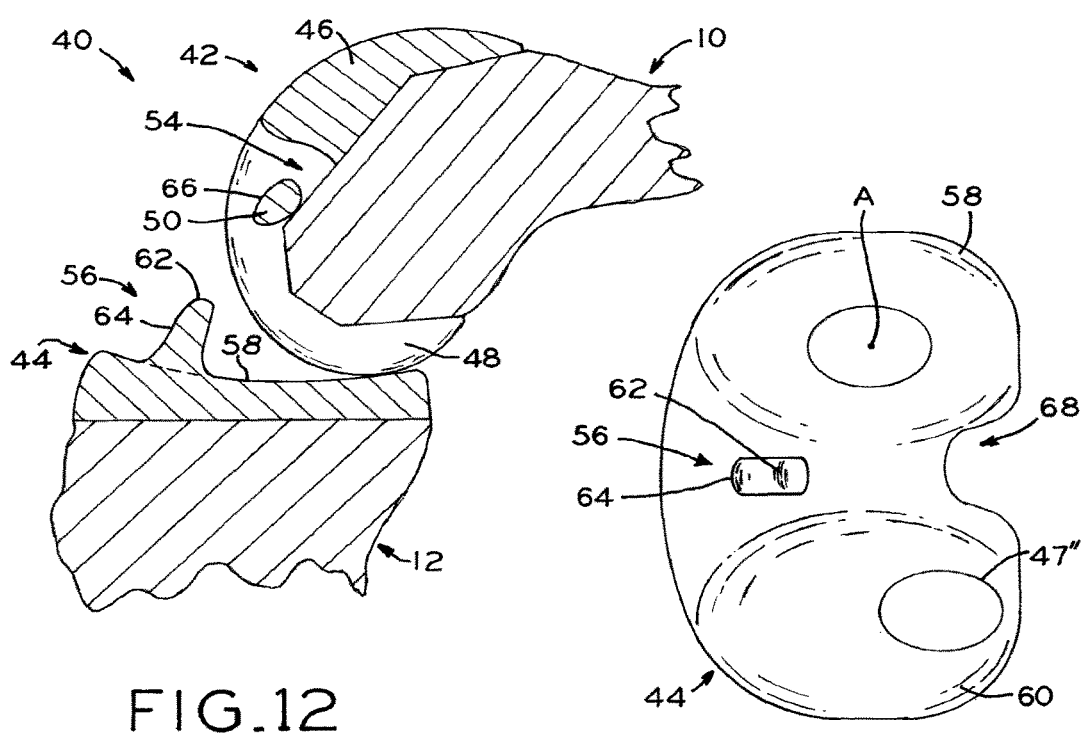
FIG. 12 is a view similar to FIG. 10 showing the knee prosthesis in a state of further flexion.
FIG. 13 is a plan view of the tibial component of FIG. 12 depicting the area of contact between the tibial component and the femoral component in the state of further flexion.

As the knee joint enters a deeper state of flexion, as shown in FIGS. 12 and 13, projection 56 may be freed from opening 54 between crossbar 50 and patello-femoral flange 46. In this flexed position, projection 56 may no longer contact crossbar 50. Once projection 56 is freed from opening 54, the relative movement between femoral component 42 and tibial component 44 becomes uninhibited. Therefore, in one exemplary embodiment, femoral component 42 may be free to rotate naturally about axis A relative to tibial component 44. Alternatively, in another exemplary embodiment, knee prosthesis 40 may incorporate some of the additional concepts disclosed herein to continue to drive rotation of femoral component 42 relative to tibial component 44 about axis A.

As the knee joint returns to extension, as shown in FIG. 8, curved proximal end 62 of projection 56 may slide back across the slanted, distal-most end 52 of patello-femoral flange 46 and/or the slanted, distal wall 66 of crossbar 50. Then, once curved proximal end 62 of projection 56 reaches the end of the distal-most end 52 of patello-femoral flange 46 and/or the distal wall 66 of crossbar 50, femoral component 42 may snap back into place atop tibial component 44. As discussed above, opening 54 may be funnel-shaped (i.e., wider at its distal end than at its proximal end) so that projection 56 is encouraged to find and enter the distal end of opening 54 as the knee joint returns to extension. As projection 56 moves toward the proximal end of opening 54, the narrowing of opening 54 helps maintain tibial component 44 in place relative to femoral component 42.

Figure 56:
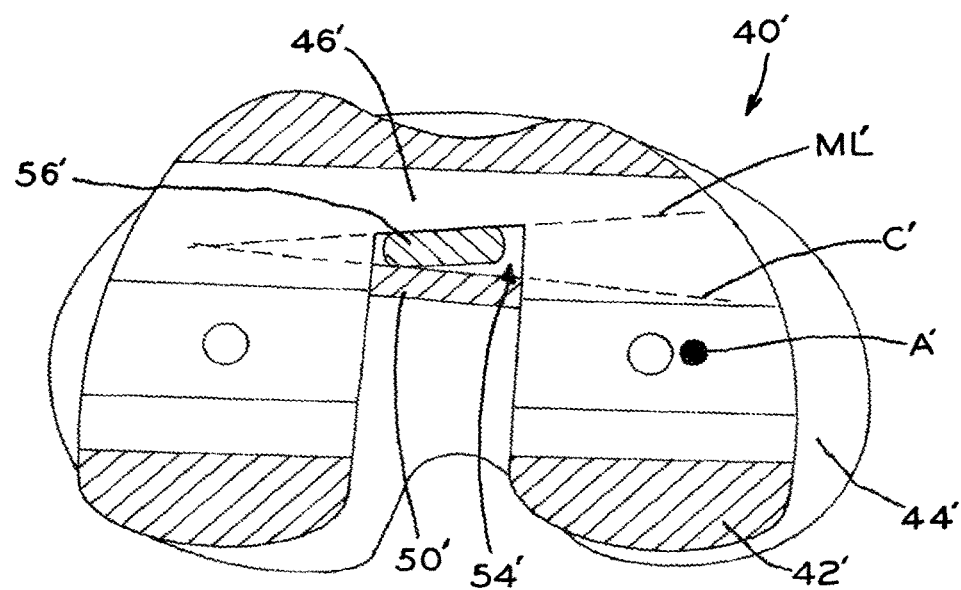
FIG. 56 is a top plan view of still yet another exemplary knee prosthesis in full extension.
Figure 57:
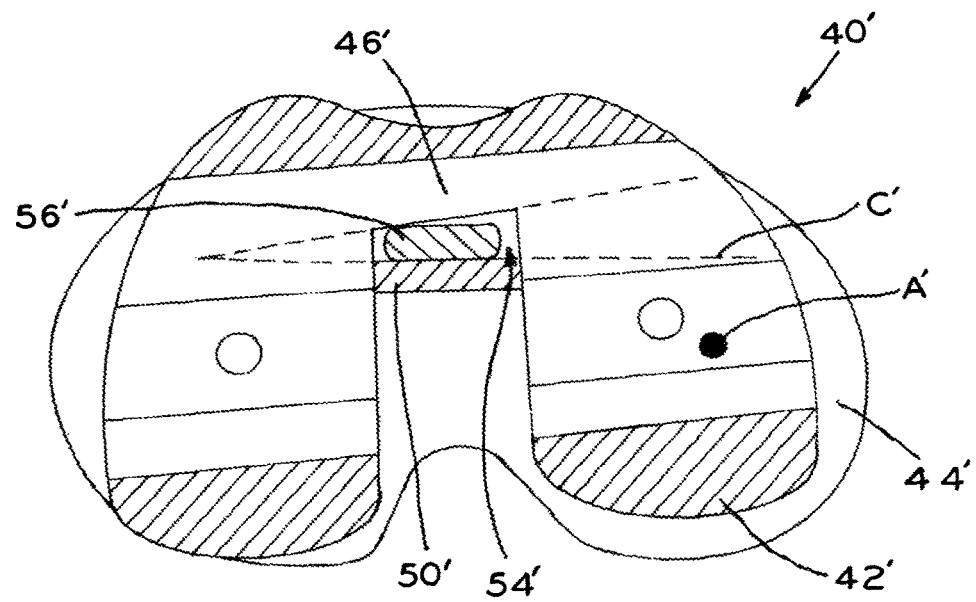
FIG. 57 is a top plan view of the knee prosthesis of FIG. 56 in early flexion.

Another exemplary knee prosthesis 40' is shown in FIGS. 56 and 57, with knee prosthesis 40' being similar to knee prosthesis 40 of FIGS. 8-13 and with like reference numerals identifying like elements. The illustrative crossbar 50' of knee prosthesis 40' extends along axis C', which deviates from medial-lateral axis ML'. With the knee joint in extension, as shown in FIG. 56, projection 56' abuts patello-femoral flange 46' to screw home and lock femoral component 42' in internal rotation relative to tibial component 44'. With the knee joint in early flexion, as shown in FIG. 57, femoral component 42' is able to rotate relative to tibial component 44' about the medially offset axis A'. As femoral component 42' rotates, projection 56' substantially disengages the patello-femoral flange 46' and instead abuts crossbar 50'. As the knee joint enters a deeper state of flexion, projection 56' may be entirely freed from opening 54' between patello-femoral flange 46' and crossbar 50' (See, e.g., FIG. 12). As discussed above with respect to knee prosthesis 40 of FIGS. 8-13, it is also within the scope of the present disclosure that the shape and/or orientation of patello-femoral flange 46' and/or projection 56' may vary in addition to or instead of crossbar 50'.

Referring next to FIGS. 14-17, another exemplary knee prosthesis 70 is shown. Knee prosthesis 70 includes femoral component 72 and tibial component 74. Femoral component 72 and tibial component 74 are implanted onto femur 10 and tibia 12, respectively, in a known manner. Knee prosthesis 70 may incorporate features of knee prosthesis 40 of FIGS. 8-13 and/or knee prosthesis 40' of FIGS. 56 and 57.

Tibial component 74 of knee prosthesis 70 may be formed in a traditional manner and includes medial and lateral articulating surfaces 76, 78, and tibial eminence 80 located therebetween. Femoral component 72 of knee prosthesis 70 may also be formed in a traditional manner and includes an anterior patello-femoral flange 82 and medial and lateral condyles 84, 86, respectively. However, unlike known femoral prostheses, medial and lateral condyles 84, 86, of femoral component 72 have, in a posterior direction, a progressively decreasing width and a progressively decreasing medial-lateral radius of curvature.

With the knee joint in extension, as shown in FIGS. 14 and 15, the portion of medial and lateral condyles 84, 86, of femoral component 72 that contacts medial and lateral articulating surfaces 76, 78, of tibial component 74 (i.e., the portion intersected by line 15-15 in FIG. 14) has a relatively large medial-lateral radius of curvature R and a relatively large width W. Therefore, as shown in FIG. 15, medial and lateral condyles 84, 86, of femoral component 72 substantially match the medial-lateral curvature of medial and lateral articulating surfaces 76, 78, of tibial component 74. Also, medial and lateral condyles 84, 86, of femoral component 72 extend substantially entirely across medial and lateral articulating surfaces 76, 78, of tibial component 74. In this extended position, the close, constrained fit between femoral component 72 and tibial component 74 prevents relative rotation between the components.

With the knee joint in flexion, as shown in FIGS. 16 and 17, the portion of medial and lateral condyles 84, 86, of femoral component 72 that contacts medial and lateral articulating surfaces 76, 78, of tibial component 74 (i.e., the portion intersected by line 17-17 in FIG. 16) has a relatively small medial-lateral radius of curvature R' (i.e., less than radius R) and a relatively small width W' (i.e., less than width W). Therefore, the contact area between femoral component 72 and tibial component 74 decreases from the extended position (FIG. 15) to the flexed position (FIG. 17). In the flexed position, the loose fit between femoral component 72 and tibial component 74 enables relative rotation between femoral component 72 and tibial component 74. For example, femoral component 72 may be free to rotate relative to tibial component 74 about axis A without impinging upon tibial eminence 80. Rather than changing the size or shape of both medial and lateral condyles 84, 86, it is also within the scope of the present disclosure that only one condyle, such as lateral condyle 86, may change size or shape. In this embodiment, medial condyle 84 may maintain close conformity with tibial component 74 to produce a medial camming action, while lateral condyle 86 may decrease in width W' and/or medial-lateral curvature R' to achieve a loose fit with tibial component 74 and to enable rotation about axis A.

Beyond the flexed position of FIGS. 16 and 17, medial and lateral condyles 84, 86, of femoral component 72 may continue to decrease in width and medial-lateral curvature.

Therefore, as femoral component 72 continues to bend posteriorly relative to tibial component 74, rotating femoral component 72 relative to tibial component 74 about axis A may become progressively easier.

Figure 18:
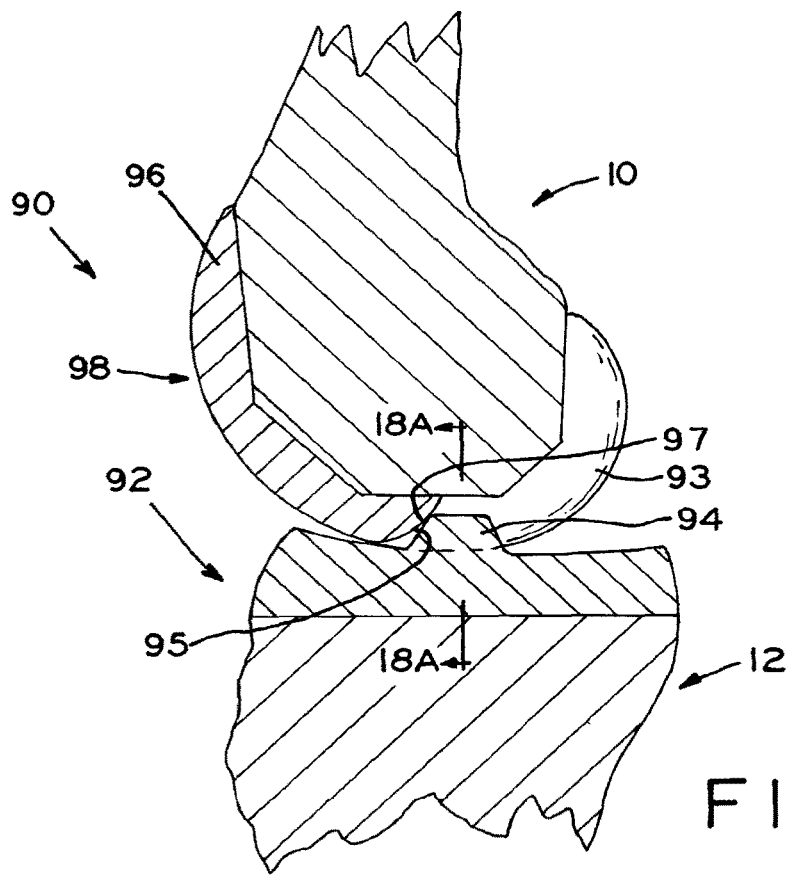
FIG. 18 is a cross-sectional view of another exemplary knee prosthesis in full extension.

Referring next to FIGS. 18-19, yet another exemplary knee prosthesis 90 is shown. Knee prosthesis 90 includes femoral component 98 and tibial component 92. Femoral component 98 and tibial component 92 are implanted onto femur 10 and tibia 12, respectively, in a known manner. Knee prosthesis 90 may incorporate features of knee prosthesis 40 of FIGS. 8-13, knee prosthesis 40' of FIGS. 56 and 57, and/or knee prosthesis 70 of FIGS. 14-17.

Femoral component 98 of knee prosthesis 40 includes an anterior patello-femoral flange 96, medial condyle 93, and an opposing lateral condyle 91. Patello-femoral flange 96 includes a distal-most end 95.

Figure 18A:
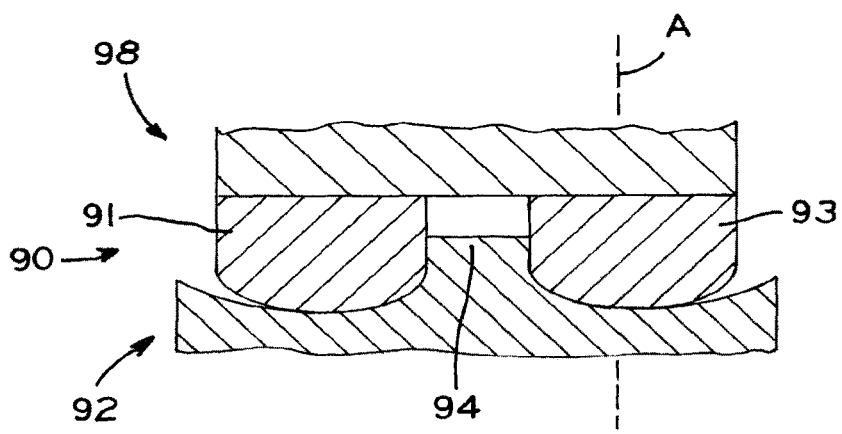
FIG. 18A is a partial, cross-sectional view of the knee prosthesis of FIG. 18, taken along line 18A-18A of FIG. 18.

Tibial component 92 of knee prosthesis 90 includes projection 94 that extends proximally from the medial-lateral midpoint of tibial component 92, as shown in FIG. 18A. Projection 94 includes anterior wall 97. As shown in FIG. 18, projection 94 is spaced slightly anteriorly of the anterior-posterior midpoint of tibial component 92. Because projection 94 terminates before reaching the posterior-most end of tibial component 92, projection 94 may avoid interfering with a patient's PCL.

With the knee joint in extension, as shown in FIGS. 18 and 18A, anterior wall 97 of projection 94 abuts the distal-most end 95 of patello-femoral flange 96 to limit anterior movement of tibia 12 relative to femur 10. Also, projection 94 extends between medial and lateral femoral condyles 93, 91, to limit rotational movement of femoral component 98 relative to tibial component 92.

With the knee joint in flexion, as shown in FIGS. 19 and 19A, the distal-most end 95 of patello-femoral flange 96 may disengage anterior wall 97 of projection 94. Also, femoral component 98 may translate posteriorly behind protrusion 94, allowing femoral component 98 to rotate naturally relative to tibial component 92 about axis A without substantially impeding upon protrusion 94.

Figure 20:
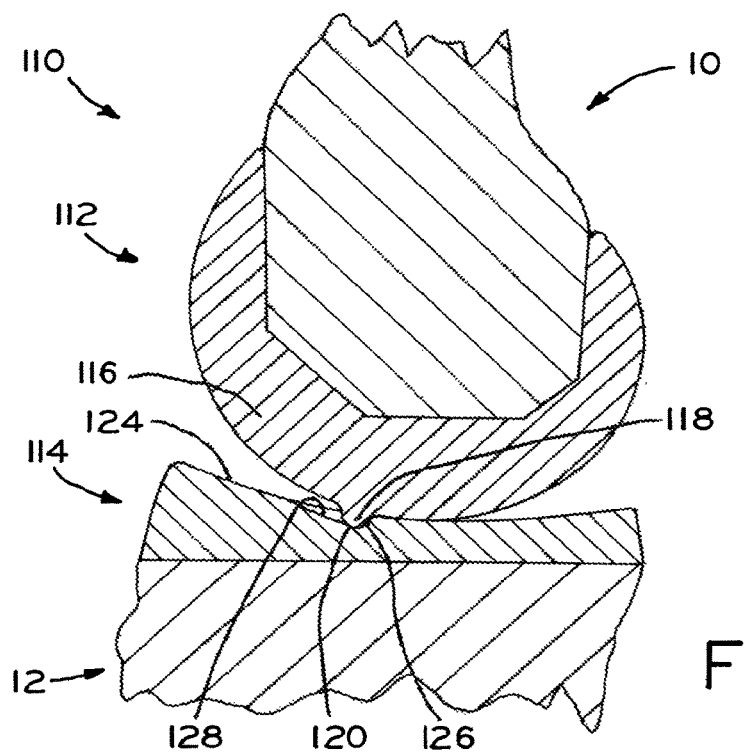
FIG. 20 is a cross-sectional view of yet another exemplary knee prosthesis in full extension.
Figure 21:
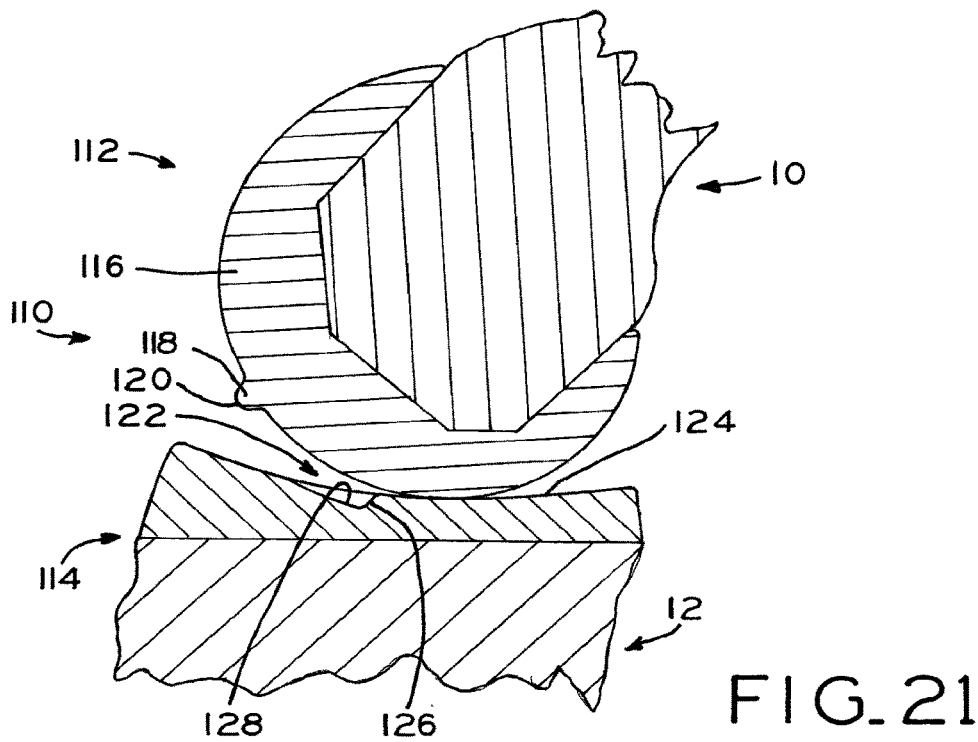
FIG. 21 is a view similar to FIG. 20 showing the knee prosthesis in early flexion.

Referring next to FIGS. 20 and 21, yet another exemplary knee prosthesis 110 is shown. Knee prosthesis 110 includes femoral component 112 and tibial component 114. Femoral component 112 and tibial component 114 are implanted onto femur 10 and tibia 12, respectively, in a known manner. Knee prosthesis 110 may incorporate features of knee prosthesis 40 of FIGS. 8-13, knee prosthesis 40' of FIGS. 56 and 57, knee prosthesis 70 of FIGS. 14-17, and/or knee prosthesis 90 of FIGS. 18-19.

Lateral condyle 116 of femoral component 112 includes projection 118 having arcuate end 120 that extends distally from lateral condyle 116. Lateral articulating surface 124 of tibial component 114 includes a corresponding recess or opening 122 that is sized to receive projection 118 from femoral component 112. As shown in FIG. 20, opening 122 is defined by posterior wall 126 and ramped surface 128 of tibial component 114. In certain embodiments, projection 118 and opening 122 may be formed at the outermost, lateral edge of femoral component 112 and tibial component 114. It is within the scope of the present disclosure that a similar projection 118 and a corresponding opening 122 may be formed on a medial condyle (not shown) of femoral component 112 and a medial articulating surface (not shown) of tibial component 114, instead of or in addition to those features formed on lateral condyle 116 and lateral articulating surface 124.

With the knee joint in extension, as shown in FIG. 20, posterior wall 126 of opening 122 in tibial component 114 abuts projection 118 of femoral component 112 to limit anterior movement of tibia 12 relative to femur 10. Then, as the knee enters a state of flexion, as shown in FIG. 21, projection 118 travels along ramped surface 128 to exit opening 122. Once in this flexed position, femoral component 112 and tibial component 114 may move relative to one another in a natural, unobstructed manner.

Referring next to FIGS. 22-24, an alternative embodiment knee prosthesis 110' is shown. Unlike opening 122 of knee prosthesis 110 which includes ramped surface 128 (FIGS. 20-21), opening 130 of knee prosthesis 110' lacks a ramped surface. In this embodiment, opening 130 includes opposing sidewalls 132, 134, that cooperate to define opening 130.

With the knee joint in extension, as shown in FIG. 20, sidewalls 132, 134, of tibial component 114' abut projection 118' of femoral component 112' to limit anterior and posterior movement of tibia 12 relative to femur 10. As the knee joint begins to enter a state of flexion, as shown in FIG. 23, projection 118' contacts anterior wall 132 of tibial component 114', which may force lateral condyle 116' of femoral component 112' in a posterior direction to a greater extent that the medial condyle (not shown) of femoral component 112'. Therefore, anterior wall 132 of tibial component 114' may drive rotation of femoral component 112'. As the knee joint continues to bend, as shown in FIG. 24, projection 118' may withdraw from opening 130 and, as a result, femoral component 112' and tibial component 114' may move relative to one another in a natural, unobstructed manner. Although projection 118' is described as being formed on lateral condyle 116' of femoral component 112' to induce translation and/or rotation of lateral condyle 116', it is also within the scope of the present disclosure that projection 118' may be formed on a medial condyle (not shown) of femoral component 112', instead of or in addition to lateral condyle 116'. In either location, projection 118' may encourage anterior movement of femoral component 112' when the knee joint transitions from flexion (FIG. 24) to extension (FIG. 22).

Referring to FIGS. 25-28, yet another exemplary knee prosthesis 140 is shown. Knee prosthesis 140 includes femoral component 142 and tibial component 144, which may be a mobile bearing tibial component. Femoral component 142 and tibial component 144 are implanted onto femur 10 and tibia 12, respectively, in a known manner. Knee prosthesis 140 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, and/or knee prosthesis 110' of FIGS. 22-24.

Figure 25:
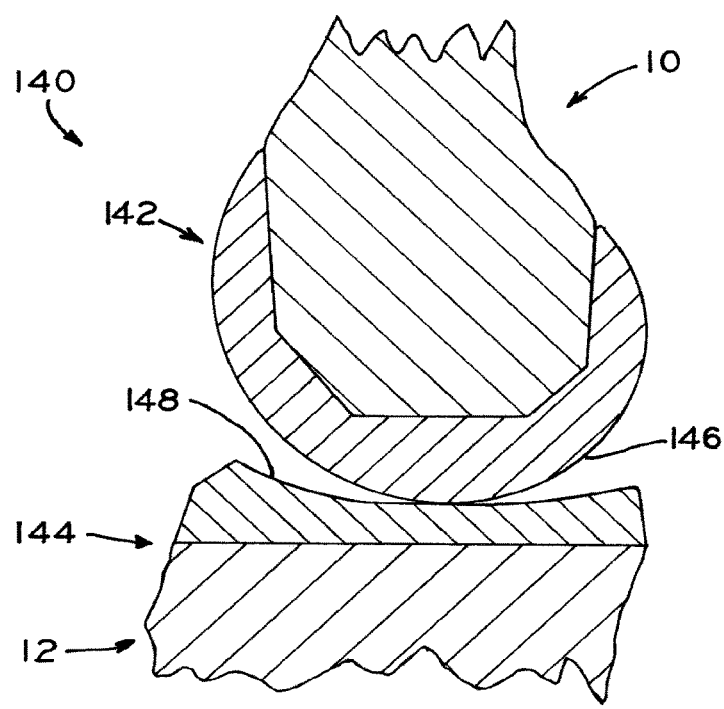
FIG. 25 is a medial cross-sectional view of yet another exemplary knee prosthesis in full extension.
Figure 26:
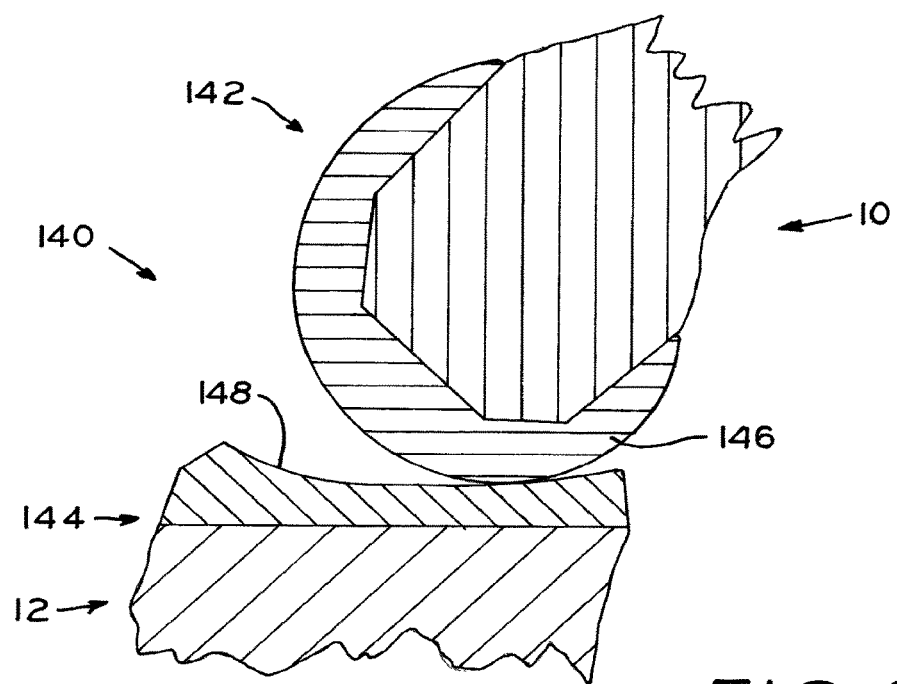
FIG. 26 is a view similar to FIG. 25 showing the knee prosthesis in early flexion.

The medial side of knee prosthesis 140 is shown in FIGS. 25 and 26. Specifically, the medial side of knee prosthesis 140 includes medial condyle 146 of femoral component 142 and medial articulating surface 148 of tibial component 144. The medial side of knee prosthesis 140 may be in the shape of a traditional cruciate-retaining prosthesis.

Figure 27:
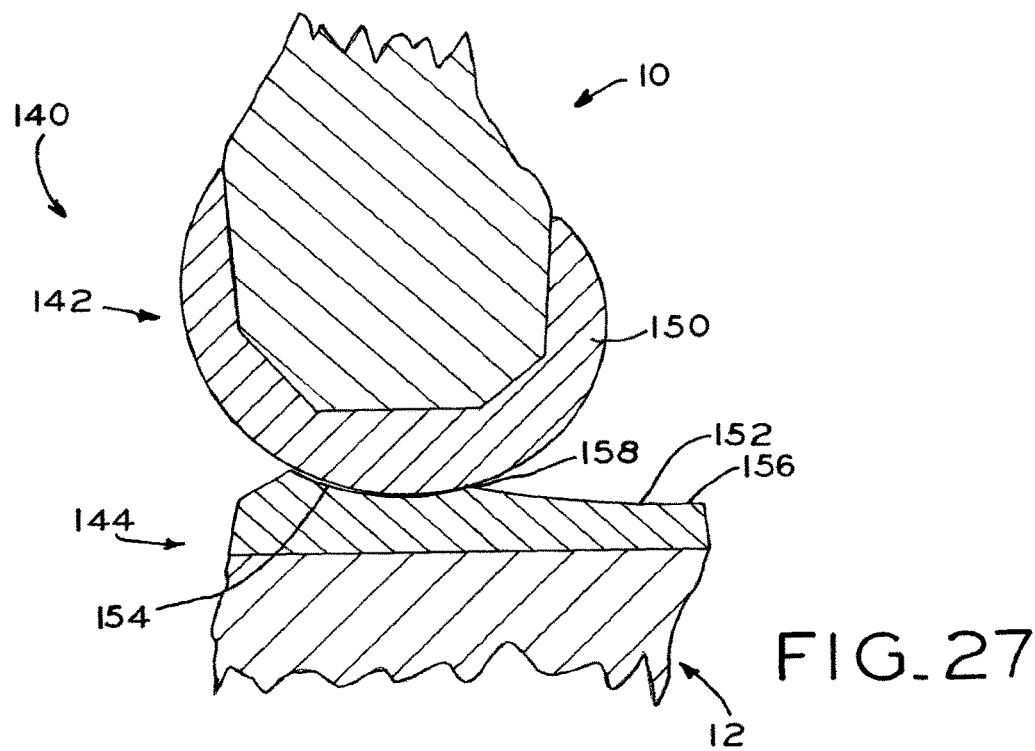
FIG. 27 is a lateral cross-sectional view of the knee prosthesis of FIG. 25.
Figure 28:
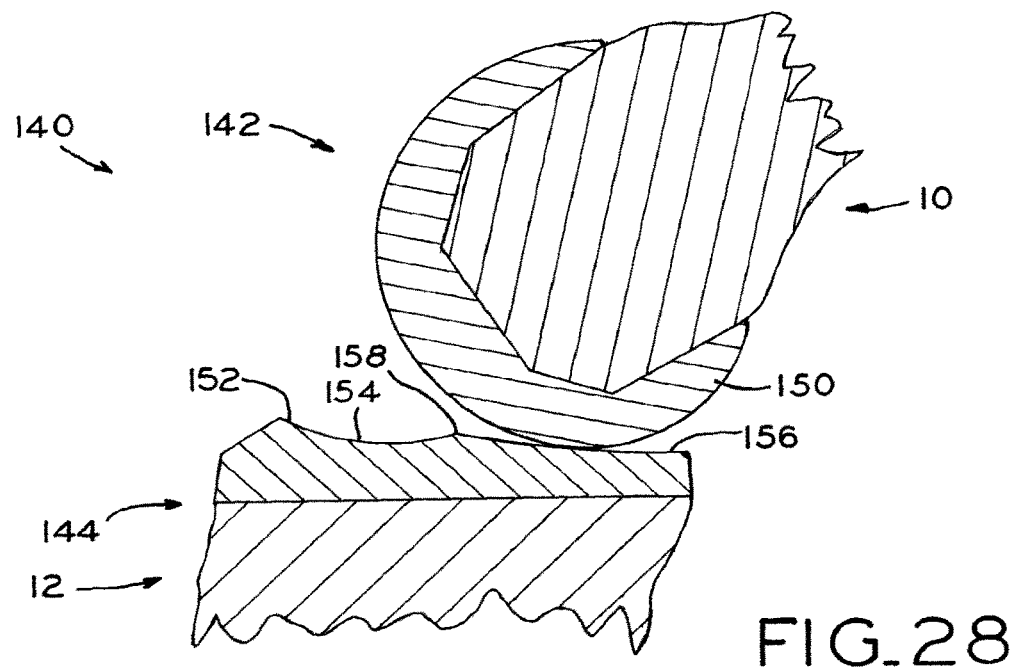
FIG. 28 is a view similar to FIG. 27 showing the knee prosthesis in early flexion.

The lateral side of knee prosthesis 140 is shown in FIGS. 27 and 28. Specifically, the lateral side of knee prosthesis 140 includes lateral condyle 150 of femoral component 142 and lateral articulating surface 152 of tibial component 144.

The lateral side of knee prosthesis 140 differs from the medial side of knee prosthesis 140. Specifically, lateral articulating surface 152 of tibial component 144 includes a first, anterior section 154 and a second, posterior section 156 separated by inflection point 158. In one exemplary embodiment, both anterior portion 154 and posterior portion 156 define substantially concave articulating surfaces. In another exemplary embodiment, anterior portion 154 defines a substantially concave or flat articulating surface, while posterior portion 156 defines a ramped articulating surface.

When the knee joint is in extension, as shown in FIG. 27, lateral condyle 150 of femoral component 142 may conform to the shape of anterior portion 154 of lateral articulating surface 152. For example, anterior portion 154 of lateral articulating surface 152 may define a concave pocket that cradles lateral condyle 150 of femoral component 142. Femoral component 142 will be held in this extended position until femoral component 142 is able to roll up and over inflection point 158.

As the knee joint enters a state of flexion, as shown in FIG. 28, lateral condyle 150 of femoral component 142 rolls across posterior portion 156 of lateral articulating surface 152. Posterior portion 156 of lateral articulating surface 152 may be sloped or curved to drive lateral condyle 150 in a posterior direction across tibial component 144. Because medial condyle 146 remains substantially in place on medial articulating surface 148 (FIG. 26), posterior portion 156 of lateral articulating surface 152 drives rotation of femoral component 142 relative to tibial component 144.

Figure 29:
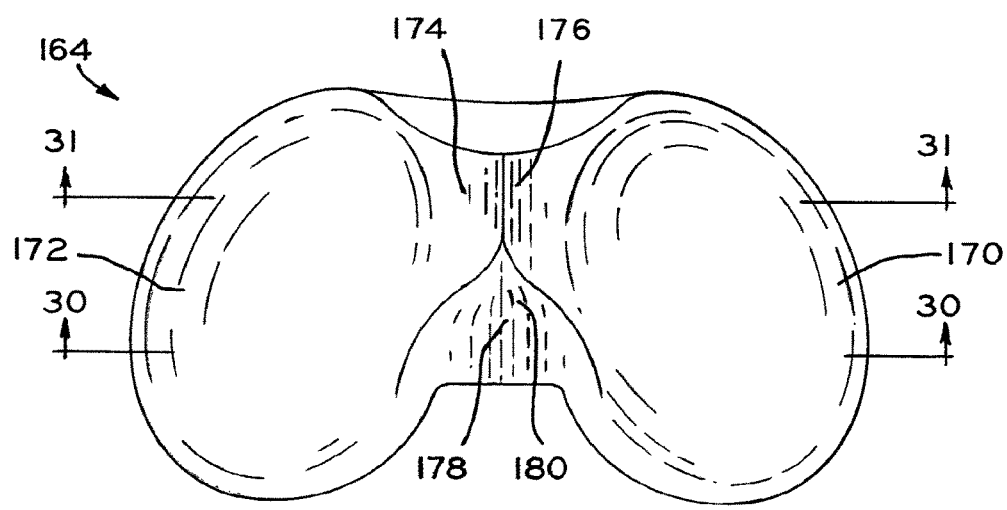
FIG. 29 is a plan view of a tibial component of yet another exemplary knee prosthesis.
Figure 30:
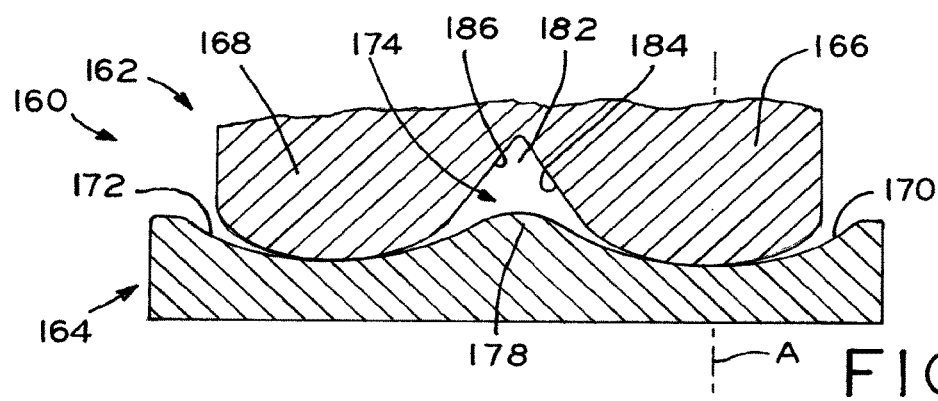
FIG. 30 is a partial, cross-sectional view of the tibial component of FIG. 29, taken along line 30-30 of FIG. 29, the knee prosthesis including a femoral component in early flexion relative to the tibial component.
Figure 31:
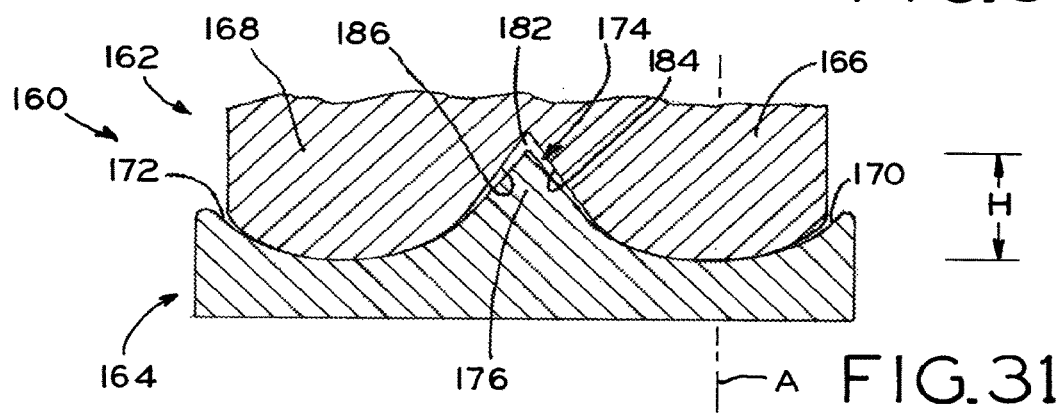
FIG. 31 is a view similar to FIG. 30 showing the knee prosthesis in full extension, taken along line 31-31 of FIG. 29.
Figure 34:
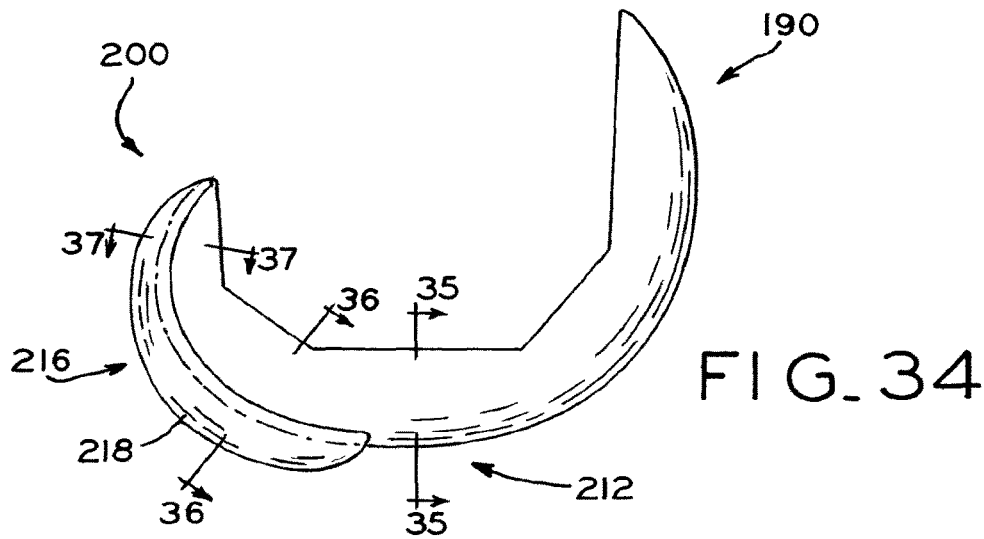
FIG. 34 is a medial, elevational view of a femoral component for use in conjunction with the tibial component of FIG. 32.
Figure 35:
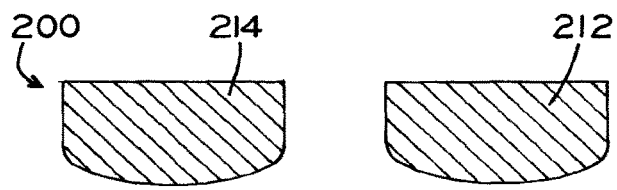
FIG. 35 is a cross-sectional view of the femoral component of FIG. 34, taken along line 35-35 of FIG. 34.
Figure 36:
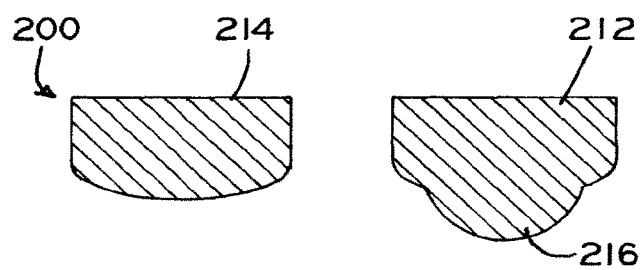
FIG. 36 is a cross-sectional view of the femoral component of FIG. 34, taken along line 36-36 of FIG. 34.
Figure 37:
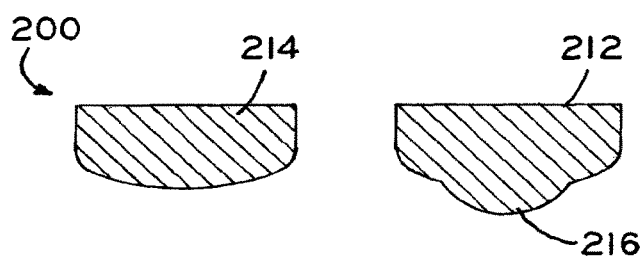
FIG. 37 is a cross-sectional view of the femoral component of FIG. 34. taken along line 37-37 of FIG. 34.

Referring to FIGS. 29-31, yet another exemplary knee prosthesis 160 is shown. Knee prosthesis 160 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, and/or knee prosthesis 140 of FIGS. 25-28.

Femoral component 162 of knee prosthesis 160 includes medial and lateral condyles 166, 168. Medial wall 184 of medial condyle 166 and lateral wall 186 of lateral condyle 168 cooperate to define a substantially triangular shaped opening 182 therebetween.

Tibial component 164 of knee prosthesis 160 includes medial and lateral articulating surfaces 170, 172. Tibial eminence 174 extends from tibial component 164 between articulating surfaces 170, 172. As shown in FIG. 31, anterior portion 176 of tibial eminence 174 has a substantially triangular cross-section. As shown in FIG. 30, posterior portion 178 of tibial eminence 174 has a rounded cross-section. Transition portion 180 of tibial eminence 174 extends between anterior portion 176 and posterior portion 178. Transition portion 180 provides for a gradual transition between the substantially triangular cross-section of anterior portion 176 and the rounded cross-section of posterior portion 178. In an anterior to posterior direction, from anterior portion 176, to transition portion 180, to posterior portion 178, tibial eminence 174 decreases in height H and flattens out (i.e., increases in radius of curvature). As a result, the sharp point on anterior portion 176 of tibial eminence 174 gradually fades away toward posterior portion 178 of tibial eminence 174.

With the knee joint in extension, as shown in FIG. 31, anterior portion 176 of tibial eminence 174 conforms tightly to the shape of opening 182 in femoral component 162. The close, constraining fit between femoral component 162 and tibial component 164 prevents relative rotation between the components.

With the knee joint in flexion, as shown in FIG. 30, posterior portion 178 of tibial eminence 174 avoids medial and lateral walls 184, 186, of femoral component 162. In this flexed position, the loose fit between femoral component 162 and tibial component 164 enables natural rotation between the components. For example, femoral component 162 may be free to rotate relative to tibial component 164 about axis A without impinging on tibial eminence 174. The loose fit between femoral component 162 and tibial component 164 may also be achieved by decreasing the width and/or the medial-lateral radius of curvature of medial and lateral condyles 166, 168, in flexion, as discussed above with reference to FIG. 17.

As the knee joint reenters extension, as shown in FIG. 31, anterior portion 176 of tibial eminence 174 may contact either or both walls 184, 186. This contact between femoral component 162 and tibial component 164 may center and align the components as they reenter extension. For example, medial and lateral walls 184, 186, will guide tibial eminence 174 into opening 182 until medial and lateral condyles 166, 168, of femoral component 162 are spaced atop and evenly situated upon medial and lateral articulating surfaces 170, 172, of tibial component 164, respectively. In this manner, tibial eminence 174 cooperates with walls 184, 186, to drive femoral component 162 into a centered or home position when the knee joint is in extension.

Referring next to FIGS. 32-37, yet another exemplary knee prosthesis 190 is shown. Knee prosthesis 190 includes femoral component 200 (FIG. 34) and tibial component 202 (FIG. 32). Knee prosthesis 190 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, and/or knee prosthesis 160 of FIGS. 29-31.

As shown in FIGS. 32 and 33, tibial component 202 of knee prosthesis 190 includes lateral articulating surface 204 and medial articulating surface 206. Lateral articulating surface 204 may be formed in any desired manner. For example, lateral articulating surface 204 may be flat, concave, or sloped. Medial articulating surface 206 includes concave outer section 208 having a first radius of curvature and concave inner section 210 having a second radius of curvature. In one exemplary embodiment, and as shown in FIG. 33, the second radius of curvature of concave inner section 210 is substantially less than the first radius of curvature 208 of concave outer section 208. As a result, concave inner section 210 forms a depression in medial articulating surface 206 relative to concave outer section 208.

As shown in FIGS. 34-37, femoral prosthesis 200 of knee prosthesis 190 includes medial condyle 212 and lateral condyle 214. As shown, lateral condyle 214 may be formed in a traditional manner and have a substantially consistent radius of curvature. In contrast, medial condyle 212 includes projection 216 that defines an area of increased thickness on the posterior portion of lateral condyle 214. In an anterior plane (FIG. 35), medial and lateral condyles 212, 214, have substantially similar cross-sections. In a more posterior plane (FIG. 36), projection 216 extends from medial condyle 212 such that medial condyle 212 is substantially increased in thickness compared to lateral condyle 214. In a further posterior plane (FIG. 37), the thickness of medial condyle 212 is decreased slightly, but projection 216 still provides medial condyle 212 with an increased thickness over lateral condyle 214.

In use, medial condyle 212 of femoral component 200 is designed to conform with medial articulating surface 206 of tibial component 202. For example, in extension, medial condyle 212 contacts shallow, outer articulating portion 208 of medial articulating surface 206 of tibial component 202. As the knee enters flexion, projection 216 of medial condyle 212 enters concave inner surface 210 of medial articulating surface 206 of tibial component 202. Specifically, projection 216 is sized such that the outer surface of projection 216 that is in contact with concave inner surface 210 during knee joint flexion is highly conforming to the wall defining concave inner surface 210 of articulating surface 206. As the knee joint continues through flexion, the interaction of projection 216 with concave inner surface 210 of articulating surface 206 may, depending on the configuration of concave inner surface 210, cause a camming action that drives rotation of femoral component 200 relative to tibial component 202 about a medially offset axis A. Specifically, projection 216 and inner surface 210 may be designed to drive rotation of lateral condyle 214 of femoral component 200 about a medially offset axis that extends through concave inner surface 210.

Figure 38:
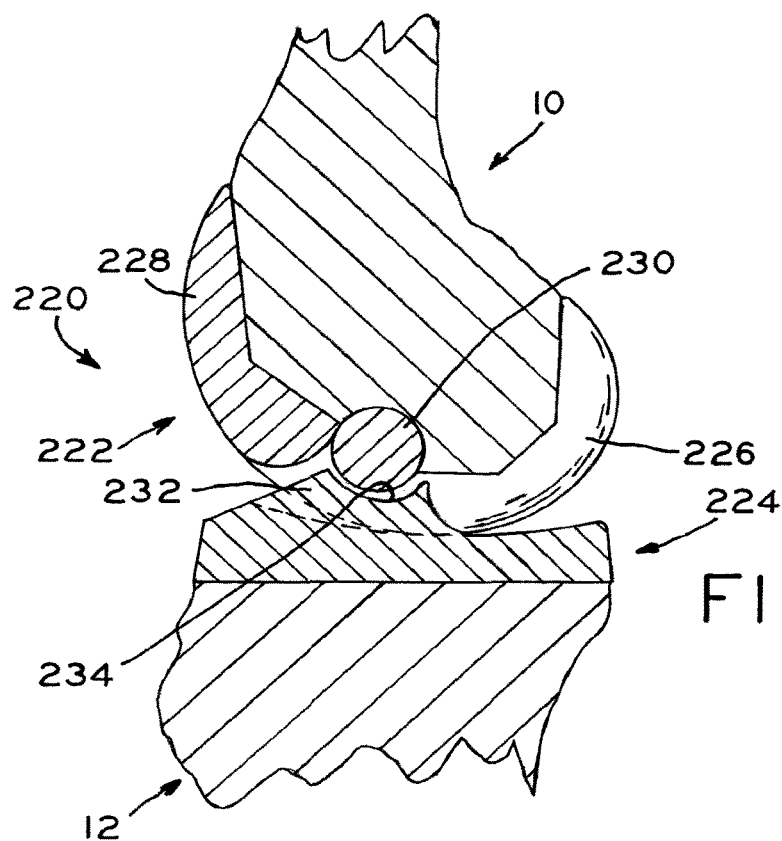
FIG. 38 is a cross-sectional view of still yet another exemplary knee prosthesis in full extension.
Figure 39:
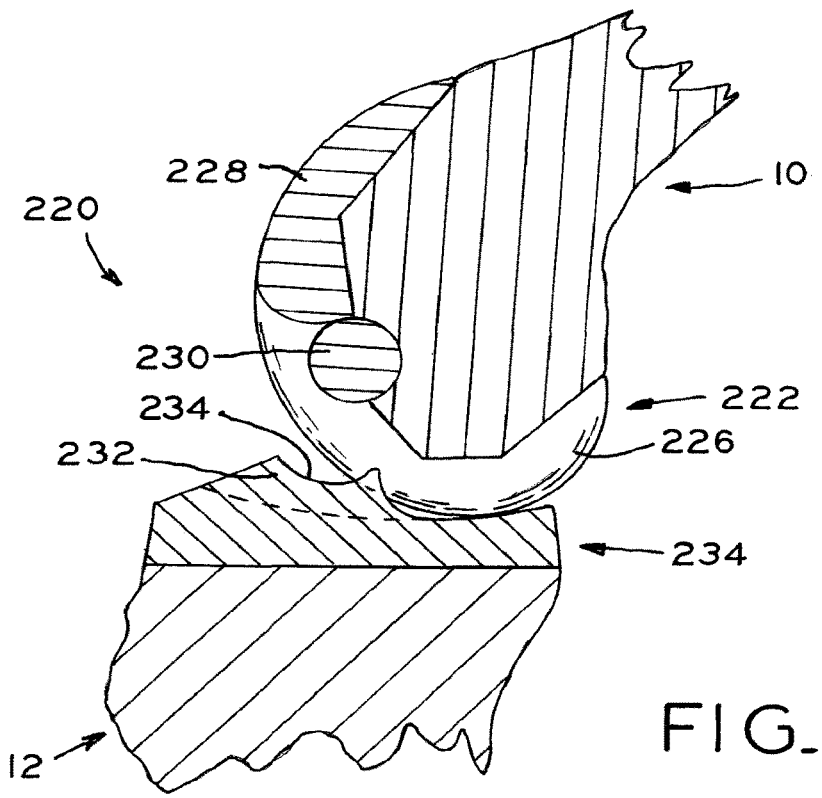
FIG. 39 is a view similar to FIG. 38 showing the knee prosthesis in early flexion.

Referring to FIGS. 38 and 39, yet another exemplary knee prosthesis 220 is shown. Knee prosthesis 220 includes femoral component 222 and tibial component 224. Knee prosthesis 220 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, and/or knee prosthesis 190 of FIGS. 32-37.

As shown in FIG. 38, femoral component 222 of knee prosthesis 220 includes medial condyle 226, patello-femoral flange 228, a lateral condyle (not shown), and crossbar 230 that extends between medial condyle 226 and the lateral condyle. Tibial component 224 of knee prosthesis 220 includes tibial eminence 232 that projects proximally from the anterior portion of tibial component 224. The illustrative crossbar 230 has a substantially circular cross-section and is configured to rest atop tibial eminence 232 of tibial component 224. It is also within the scope of the present disclosure that crossbar 230 and/or tibial eminence 232 may change shape and/or orientation in a medial-lateral direction to force the lateral condyle (not shown) of femoral component 222 to rotate about axis A. For example, crossbar 230 and/or tibial eminence 232 may be conical in shape in the medial-lateral direction. Tibial eminence 232 includes a substantially concave upper surface 234 having a radius of curvature that is slightly less than the radius of crossbar 230.

With the knee joint in extension, as shown in FIG. 38, crossbar 230 rests atop upper surface 234 of tibial eminence 232. To reduce wear of tibial eminence 232, crossbar 230 may hover slightly above the concave upper surface 234 when the knee joint is in extension, abutting the anterior and posterior ends of upper surface 234 of tibial eminence 232 only when necessary to limit anterior and posterior movement of tibia 12 relative to femur 10. It is also within the scope of the present disclosure that crossbar 230 may fit snugly against tibial eminence 232 for more constraint against anterior and posterior movements. In addition to limiting anterior and posterior movements of tibia 12 relative to femur 10 when the knee joint is in extension, crossbar 230 and tibial eminence 232 may also cooperate to limit rotation of tibia 12 relative to femur 10.

As the knee enters flexion, as shown in FIG. 39, crossbar 230 separates from upper surface 234 of tibial eminence 232. In this flexed position, femoral component 222 and tibial component 224 may move relative to one another in a natural, unobstructed manner. For example, the remaining ligaments in the knee joint may drive rotation of femoral component 222 relative to tibial component 224.

Figure 40:
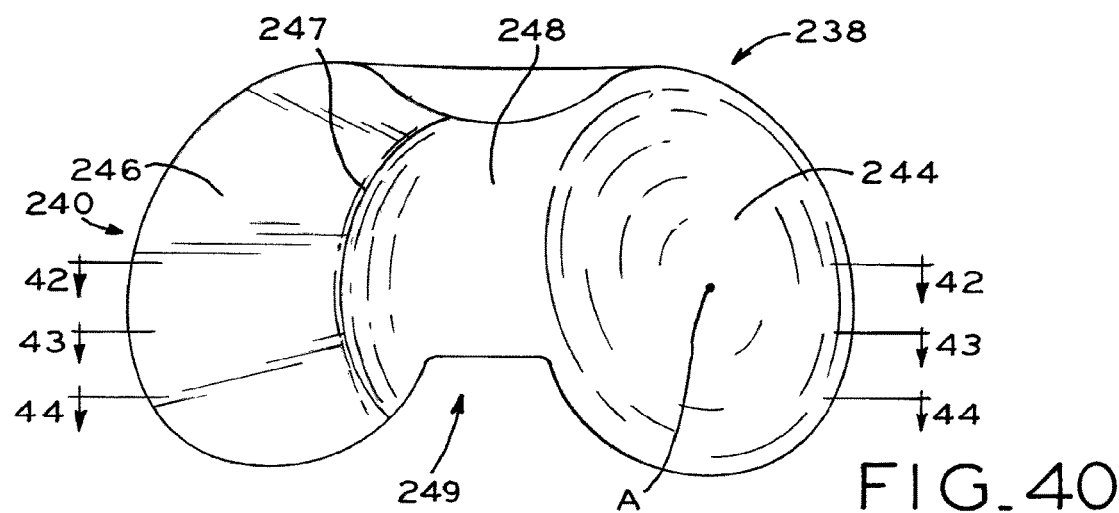
FIG. 40 is a plan view of a tibial component of yet another exemplary knee prosthesis.
Figure 41:
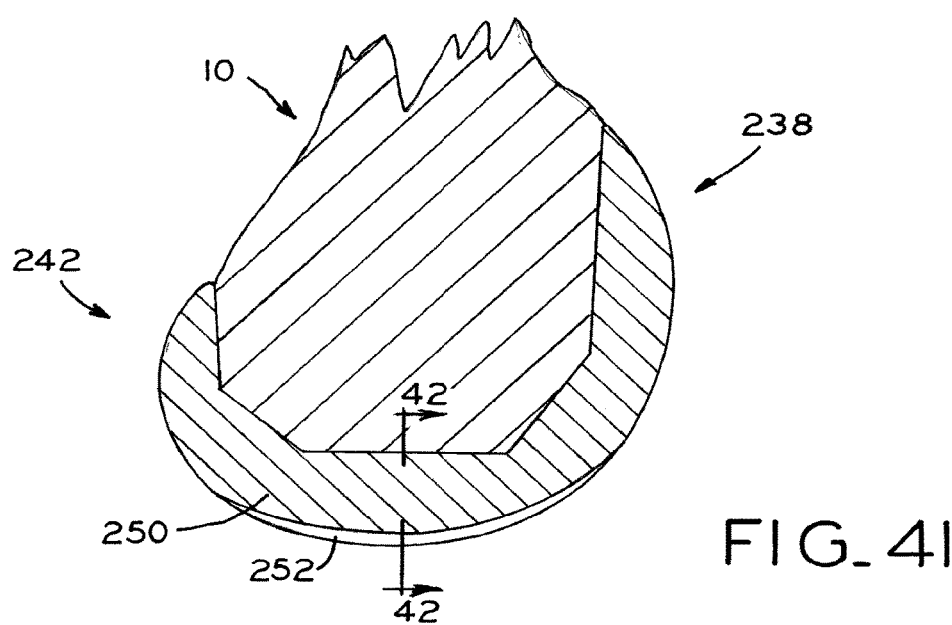
FIG. 41 is a cross-sectional view of a femoral component for use in conjunction with the tibial component of FIG. 40.

Referring to FIGS. 40-44, yet another exemplary knee prosthesis 238 is shown. Knee prosthesis 238 includes tibial component 240 (FIG. 40) and femoral component 242 (FIG. 41). Knee prosthesis 238 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, knee prosthesis 190 of FIGS. 32-37, and/or knee prosthesis 220 of FIGS. 38 and 39.

Figure 42:
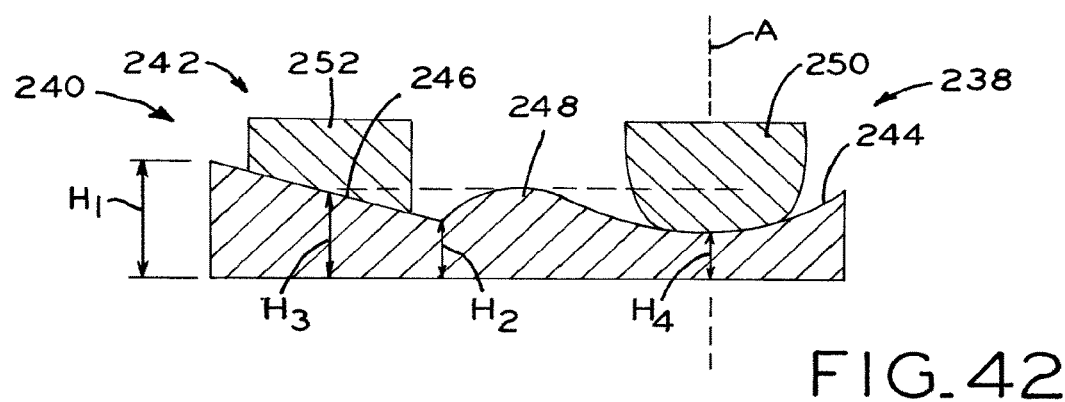
FIG. 42 is a cross-sectional view of the tibial component of FIG. 40, taken along line 42-42 of FIG. 40, and the femoral component of FIG. 41, taken along line 42-42 of FIG. 41.

As shown in FIGS. 40 and 42, tibial component 240 of knee prosthesis 238 includes medial and lateral articulating surfaces 244, 246. In a coronal plane, medial articulating surface 244 is more concave than lateral articulating surface 246. While medial articulating surface 244 forms a substantially concave surface, lateral articulating surface 246 forms a substantially planar surface that slants downwardly in a medial direction toward tibial eminence 248. For example, tibial component 240 has a height $H_1$ along its lateral edge and a height $H_2$ that is less than height $H_1$ near tibial eminence 248. Lateral articulating surface 246 also forms a generally arcuate path 247 about a medially offset axis A. Tibial component 240 may include posterior cutout 249 that is sized to receive the retained posterior cruciate ligament.

As shown in FIGS. 41 and 42, femoral component 242 of knee prosthesis 238 includes medial condyle 250 and lateral condyle 252. The medial-lateral radius of curvature of medial condyle 250 is substantially similar to the medial-lateral radius of curvature of medial articulating surface 244 of tibial component 240. Lateral condyle 252 has an articulating surface that is slanted, with or without a slightly concave curvature, in a manner that allows the articulating surface of lateral condyle 252 to maintain contact with lateral articulating surface 246 of tibial component 240.

Figure 42A:
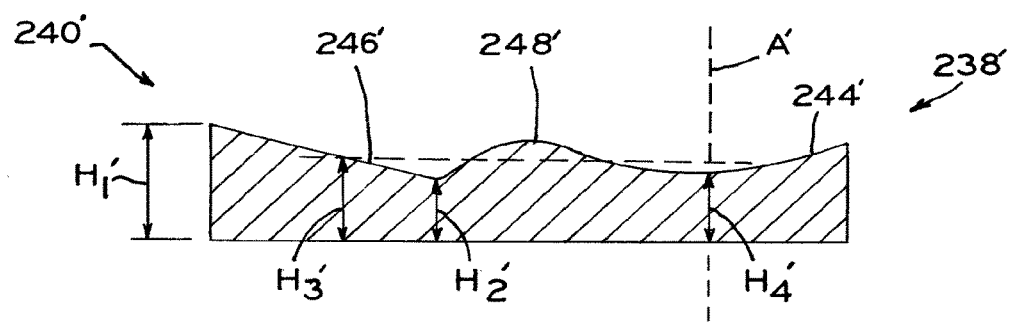
FIG. 42A is an alternative cross-sectional view of the tibial component of FIG. 40, taken along line 42-42 of FIG. 40.

When the knee joint is in an extended position, as shown in FIG. 42, the lateral height $H_1$ of lateral articulating surface 246 may exceed the medial height $H_2$ of lateral articulating surface 246. In this embodiment, femoral component 242 may be biased medially toward tibial eminence 248 and toward the medially offset axis A. In other words, the tall lateral edge of tibial component 240 (along lateral height $H_1$) may constrain lateral movement of femoral component 242 relative to tibial component 240. As shown in FIG. 42, the central height $H_3$ of lateral articulating surface 246 exceeds the central height $H_4$ of medial articulating surface 248 to further bias femoral component 242 medially toward the medially offset axis A. It is also within the scope of the present disclosure, as shown in FIG. 42A, that the central height $H_3'$ of lateral articulating surface 246' may be approximately equal to the central height $H_4'$ of medial articulating surface 248'.

Figure 43:
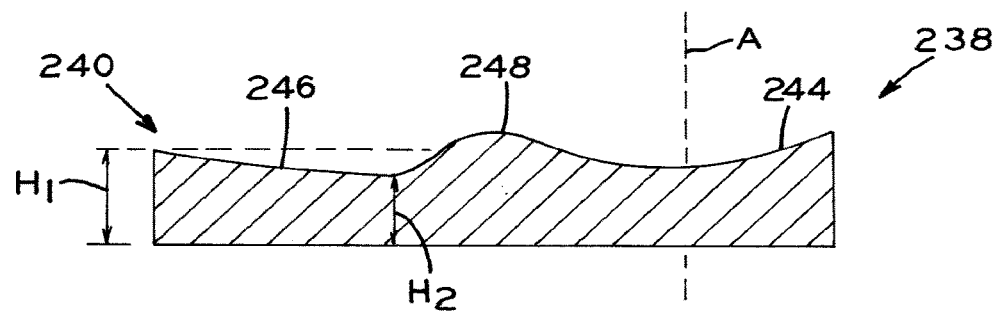
FIG. 43 is a cross-sectional view of the tibial component of FIG. 40, taken along line 43-43 of FIG. 40.
Figure 44:
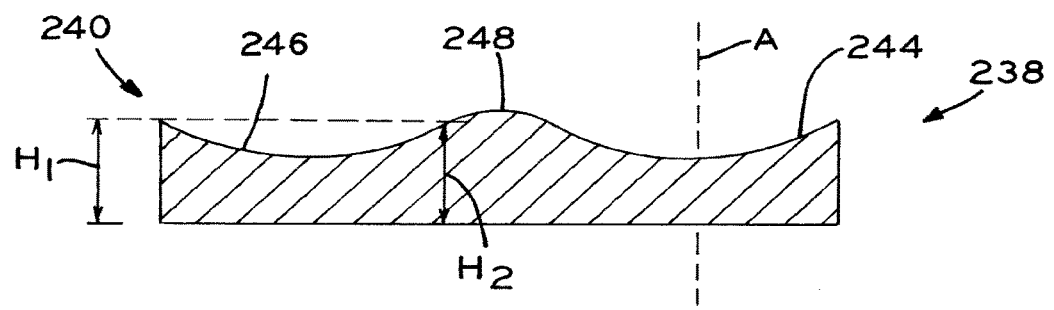
FIG. 44 is a cross-sectional view of the tibial component of FIG. 40, taken along line 44-44 of FIG. 40.

As the knee joint enters into flexion, femoral component 242 will roll back in a posterior direction. As shown in FIGS. 43 and 44, the lateral height $H_1$ of lateral articulating surface 246 may decrease in a posterior direction (i.e. posterior to section line 42-42 of FIG. 40) such that femoral component 242 is less constrained against lateral movement in the flexed position (FIGS. 43 and 44) than in the extended position (FIG. 42). This transition may occur gradually, with lateral articulating surface 246 gradually decreasing in slope until reaching a substantially horizontal surface or a slightly concave surface, as shown in FIG. 44.

Figure 45:
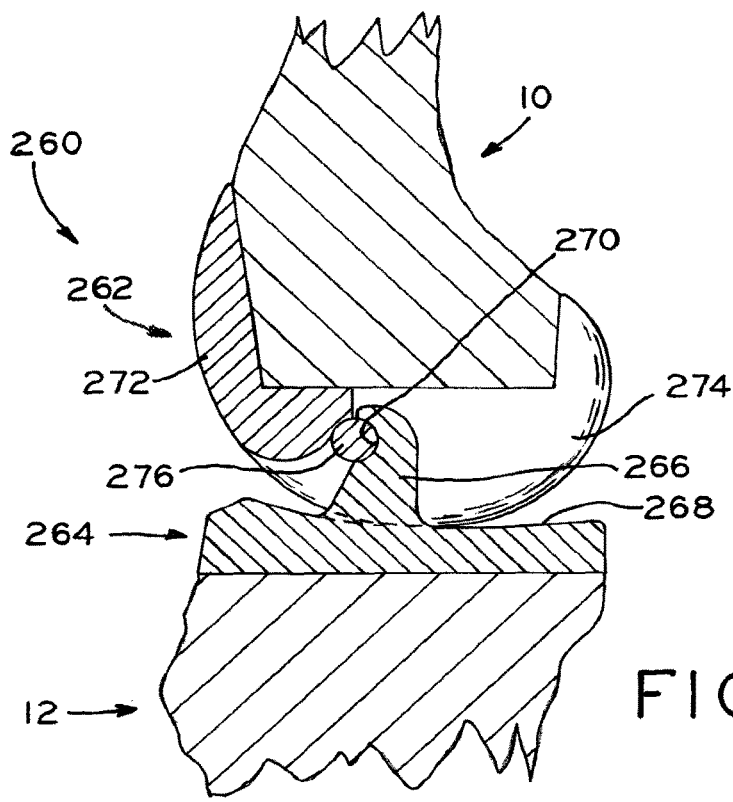
FIG. 45 is a cross-sectional view of still yet another exemplary knee prosthesis in full extension.
Figure 46:
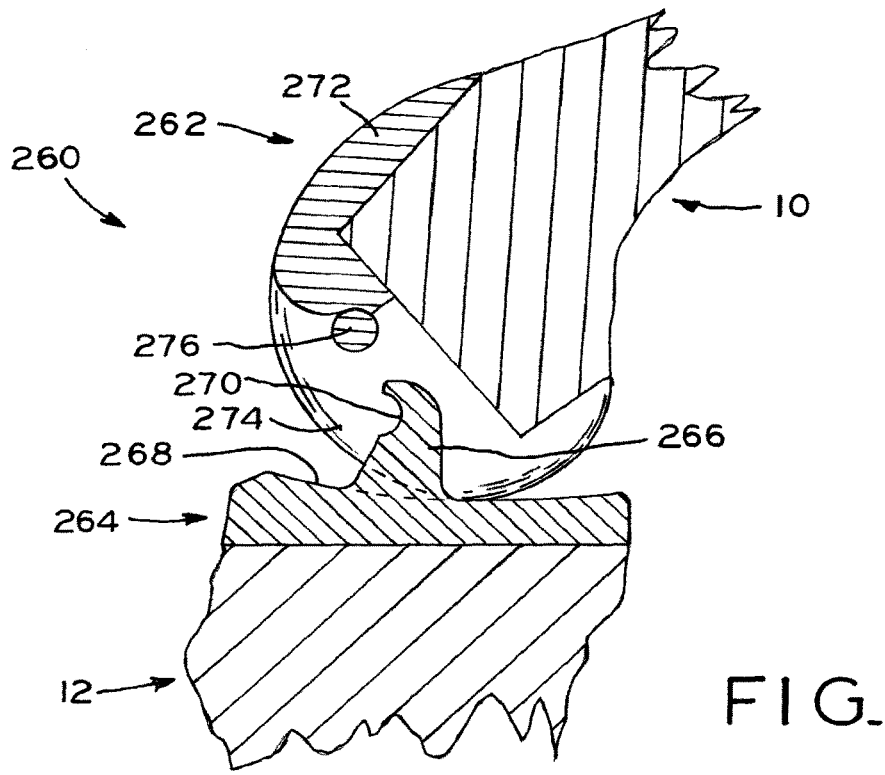
FIG. 46 is a view similar to FIG. 45 showing the knee prosthesis in early flexion.
Figure 47:
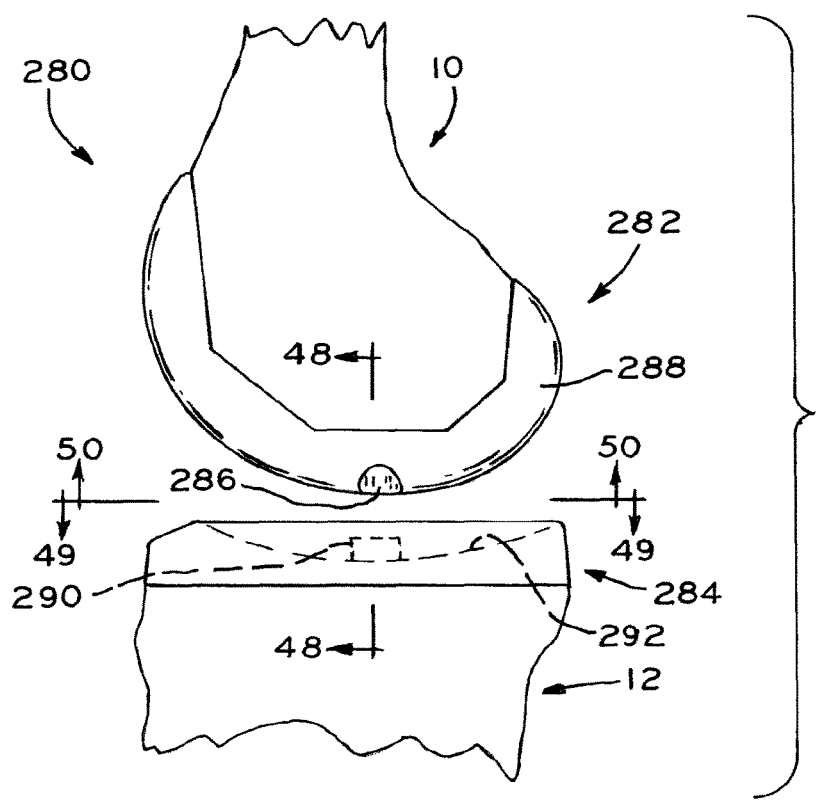
FIG. 47 is a lateral, elevational view of still yet another exemplary knee prosthesis in full extension, the knee prosthesis including a femoral component and a tibial component.

Referring next to FIGS. 45 and 46, yet another exemplary knee prosthesis 260 is shown. Knee prosthesis 260 includes femoral component 262 and tibial component 264. Knee prosthesis 260 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS.

25-28, knee prosthesis 160 of FIGS. 29-31, knee prosthesis 190 of FIGS. 32-37, knee prosthesis 220 of FIGS. 38 and 39, and/or knee prosthesis 238 of FIGS. 40-44.

Tibial component 264 of knee prosthesis 260 includes projection 266 extending upwardly therefrom between medial articulating surface 268 and an opposing lateral articulating surface (not shown). Projection 266 includes convex recess 270 formed therein.

Femoral component 262 of knee prosthesis 260 includes patello-femoral flange 272, medial condyle 274, and a lateral condyle (not shown). Crossbar 276 extends between medial condyle 274 and the lateral condyle of femoral component 262. The illustrative crossbar 276 has a substantially circular cross-section and is sized for substantially conforming receipt within recess 270 of projection 266. It is also within the scope of the present disclosure that projection 266 and/or crossbar 276 may change shape and/or orientation in a medial-lateral direction to force the lateral condyle (not shown) of femoral component 262 to rotate about axis A.

With the knee joint in extension, as shown in FIG. 45, crossbar 276 is received within recess 270 of projection 266 in a substantially conforming relationship. Projection 66 abuts crossbar 276 to prevent anterior movement of tibia 12 relative to femur 10.

As the knee joint reaches a state of flexion, as shown in FIG. 46, crossbar 276 disengages from projection 270. In this flexed position, femoral component 262 and tibial component 264 may move relative to one another in a natural, unobstructed manner. For example, the remaining ligaments in the knee joint may drive rotation of femoral component 262 relative to tibial component 264.

Referring next to FIGS. 47-50, yet another exemplary knee prosthesis 280 is shown. Knee prosthesis 280 includes femoral component 282 and tibial component 284. Knee prosthesis 280 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, knee prosthesis 190 of FIGS. 32-37, knee prosthesis 220 of FIGS. 38 and 39, knee prosthesis 238 of FIGS. 40-44, and/or knee prosthesis 260 of FIGS. 45 and 46.

Femoral component 282 of knee prosthesis 280 includes lateral condyle 288 and projection 286 extending from a lateral-most side of lateral condyle 288. Tibial component 284 of knee prosthesis 280 includes lateral articulating surface 292 and recess 290. Projection 286 of femoral component 282 is sized and shaped for receipt within recess 290 of tibial component 284.

Figure 48:
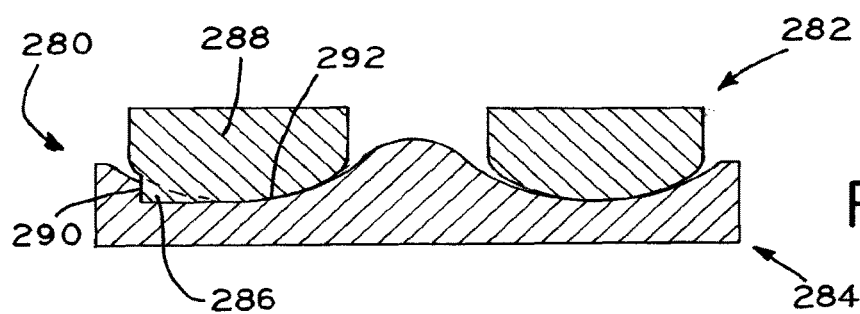
FIG. 48 is a partial cross-sectional view of the knee prosthesis of FIG. 47, taken along line 48-48 of FIG. 47.
Figure 49:
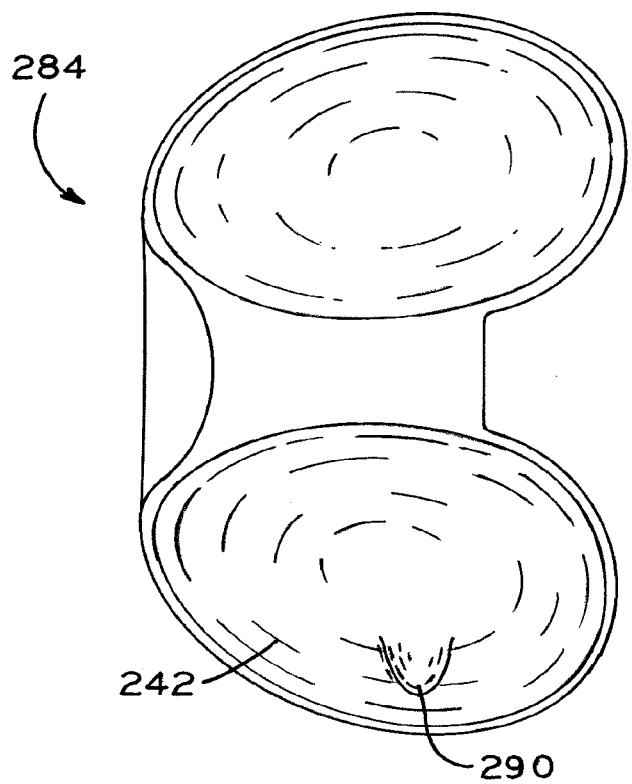
FIG. 49 is a top plan view of the tibial component of FIG. 47, taken along line 49-49 of FIG. 47.
Figure 50:
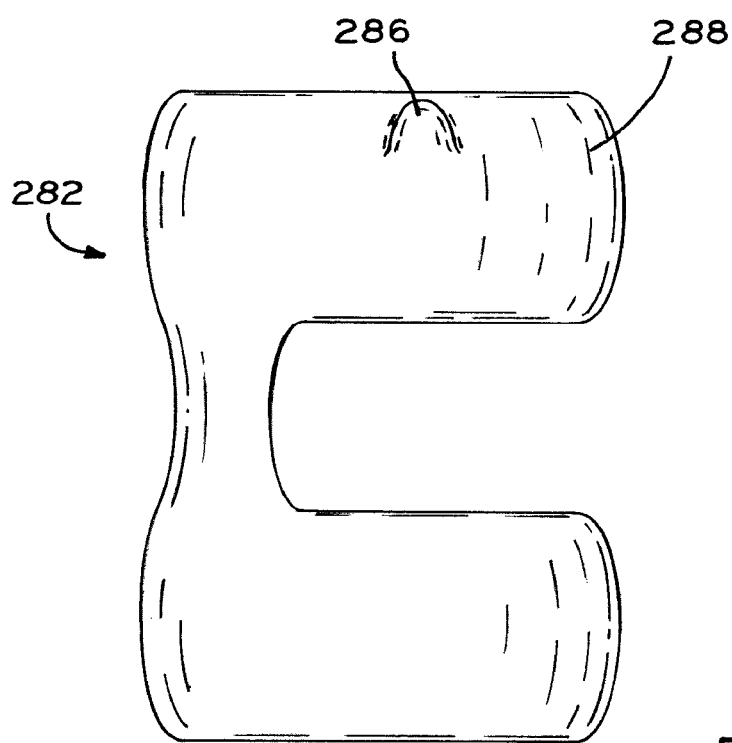
FIG. 50 is a bottom plan view of the femoral component of FIG. 47, taken along line 50-50 of FIG. 47.

With the knee joint in extension, as shown in FIG. 48, projection 286 is received within recess 290 to limit movement of femur 10 relative to tibia 12. However, as the knee joint enters flexion, projection 286 exits from recess 290, allowing femoral component 282 and tibial component 284 to move relative to one another in a natural, unobstructed manner.

Figure 51:
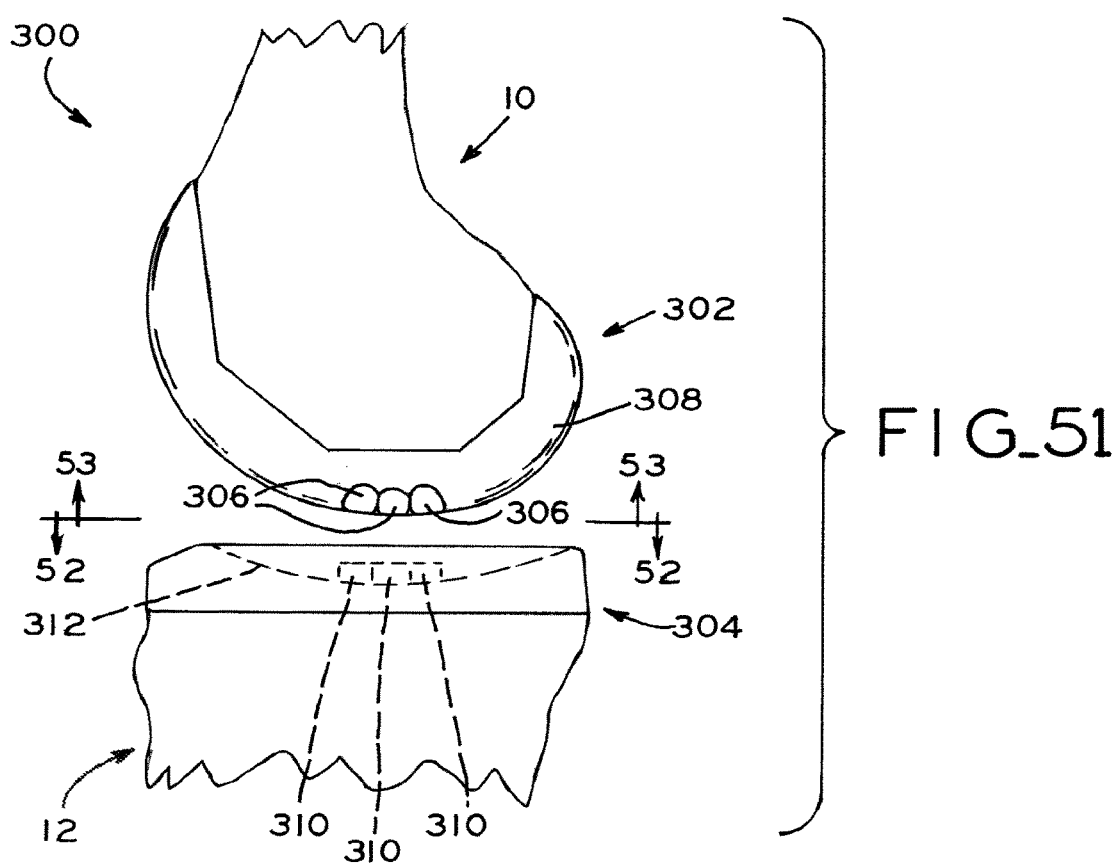
FIG. 51 is a lateral, elevational view of still yet another exemplary knee prosthesis in full extension, the knee prosthesis including a femoral component and a tibial component.
Figure 52:
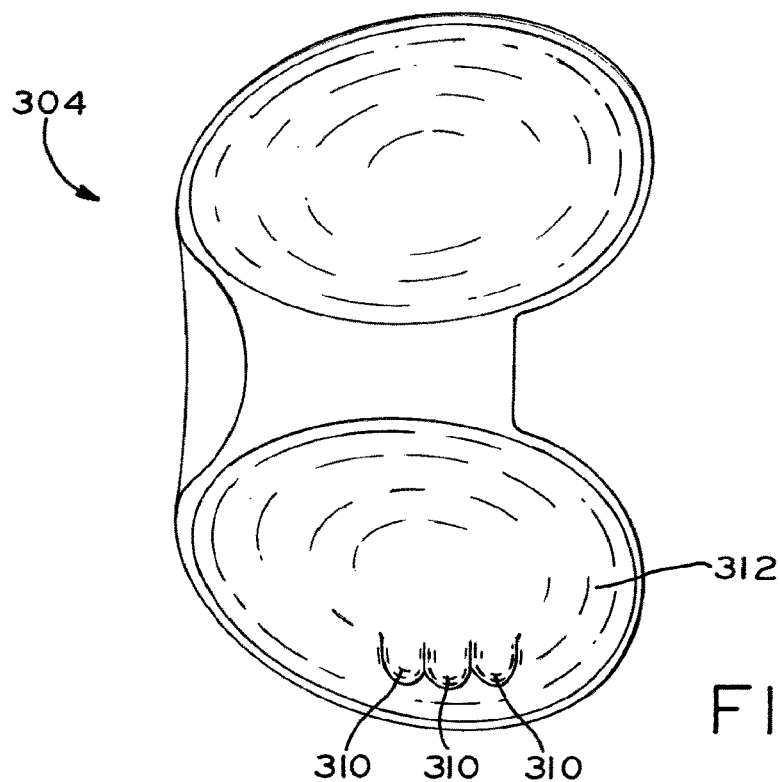
FIG. 52 is a top plan view of the tibial component of FIG. 51, taken along line 52-52 of FIG. 51.
Figure 53:
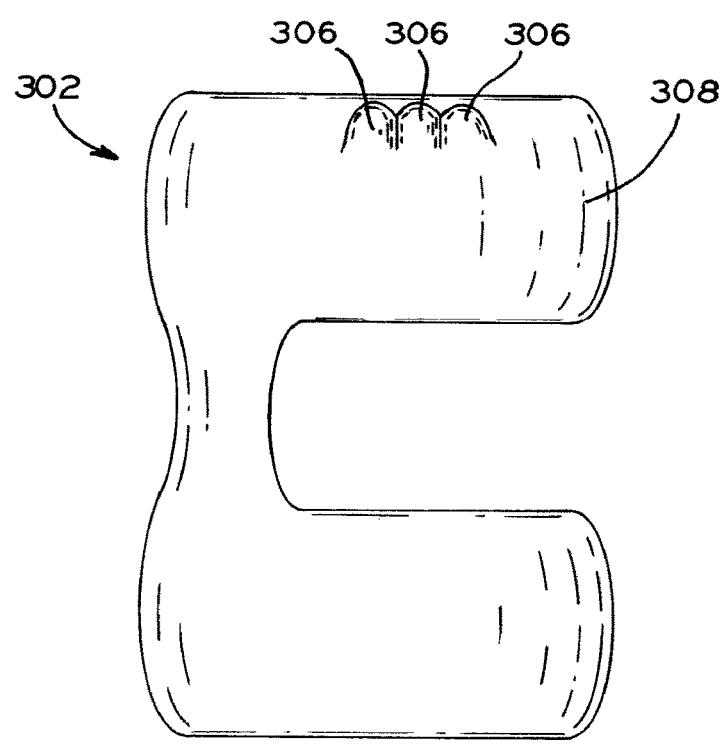
FIG. 53 is a bottom plan view of the femoral prosthesis of FIG. 51, taken along line 53-53 of FIG. 51.

Referring next to FIGS. 51-53, still yet another exemplary knee prosthesis 300 is shown. Knee prosthesis 300 includes femoral component 302 and tibial component 304. Knee prosthesis 300 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, knee prosthesis 190 of FIGS. 32-37, knee prosthesis 220 of FIGS. 38 and 39, knee prosthesis 238 of FIGS. 40-44, knee prosthesis 260 of FIGS. 45 and 46, and/or knee prosthesis 280 of FIGS. 47-50.

Knee prosthesis 300 may be substantially similar to knee prosthesis 280 of FIGS. 47-50. However, unlike knee prosthesis 280 of FIGS. 47-50, knee prosthesis 300 of FIGS. 51-53 includes a plurality of projections 306 extending from lateral condyle 308 of femoral component 302 and a plurality of recesses 310 formed in lateral articulating surface 312 of tibial component 304. By providing a plurality of projections 306 and corresponding recesses 310, knee prosthesis may lock in place in the extended position as long as any one of the projections 306 engages an adjacent recess 310. Therefore, knee prosthesis 300 may provide some flexibility in the relative positions of femoral component 302 and tibial component 304, while still achieving a stable extended position.

Referring finally to FIGS. 54 and 55, still yet another exemplary knee prosthesis 320 is shown. Knee prosthesis 320 includes femoral component 322 and tibial component 324. Knee prosthesis 320 may incorporate features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, knee prosthesis 190 of FIGS. 32-37, knee prosthesis 220 of FIGS. 38 and 39, knee prosthesis 238 of FIGS. 40-44, knee prosthesis 260 of FIGS. 45 and 46, knee prosthesis 280 of FIGS. 47-50, and/or knee prosthesis 300 of FIGS. 51-53.

Femoral component 322 of knee prosthesis 320 includes medial condyle 326 and a lateral condyle (not shown). As shown in FIG. 54, medial condyle 326 includes a substantially concave anterior portion 328 and a substantially convex posterior portion 330. It is within the scope of the present disclosure that the lateral condyle (not shown) may be shaped as shown in FIG. 54, while medial condyle 326 may be entirely convex. It is also within the scope of the present disclosure that both the lateral condyle (not shown) and medial condyle 326 may be shaped as shown in FIG. 54.

Tibial component 324 of knee prosthesis 320 includes medial articulating surface 332 and a corresponding lateral articulating surface (not shown). Medial articulating surface 332 has a substantially convex anterior portion 334 and a substantially concave posterior portion 336. Convex anterior portion 334 of medial articulating surface 332 of tibial component 324 corresponds in curvature to concave anterior portion 328 of medial condyle 326 of femoral component 322. Similarly, concave posterior portion 336 of medical articulating surface 332 of tibial component 324 corresponds in curvature to convex posterior portion 330 of medial condyle 326 of femoral component 322.

With the knee joint in extension, as shown in FIG. 54, femoral component 322 bears primarily against convex anterior portion 334 of tibial component 324, with concave anterior portion 328 of medial condyle 326 resting against convex anterior portion 334 of medial articulating surface 332. These surfaces cooperate to limit movement anterior movement of tibia 12 relative to femur 10. As a result, knee prosthesis 320 provides additional stability to the knee joint when the knee joint is in extension.

As the knee joint enters flexion, as shown in FIG. 55, concave anterior portion 328 of medial condyle 236 disengages convex anterior portion 334 of tibial component 324, allowing the remaining ligaments in the knee joint to drive rotation of femoral component 322 relative to tibial component 324. Femoral component 322 bears primarily against concave posterior portion 336 of tibial component 324, with convex posterior portion 330 of medial condyle 326 resting against concave posterior portion 336 of medial articulating surface 332.

As discussed above, it is within the scope of the present disclosure to combine features of knee prosthesis 40 of FIGS. 8-13, knee prosthesis 40' of FIGS. 56 and 57, knee prosthesis 70 of FIGS. 14-17, knee prosthesis 90 of FIGS. 18-19, knee prosthesis 110 of FIGS. 20 and 21, knee prosthesis 110' of FIGS. 22-24, knee prosthesis 140 of FIGS. 25-28, knee prosthesis 160 of FIGS. 29-31, knee prosthesis 190 of FIGS. 32-37, knee prosthesis 220 of FIGS. 38 and 39, knee prosthesis 238 of FIGS. 40-44, knee prosthesis 260 of FIGS. 45 and 46, knee prosthesis 280 of FIGS. 47-50, knee prosthesis 300 of FIGS. 51-53, and/or knee prosthesis 320 of FIGS. 54 and 55. Specifically, it is within the scope of the present disclosure to combine an intercondylar feature of one of the disclosed knee prostheses with a condylar feature of another one of the disclosed knee prostheses. Also, it is within the scope of the present disclosure to combine an anterior stabilizing feature of one of the disclosed knee prostheses with a rotation-driving feature of another one of the disclosed knee prostheses. For example, an exemplary knee prosthesis may include the anterior stabilizing feature of knee prosthesis 220 of FIGS. 38 and 39 (i.e., crossbar 230 and tibial eminence 232) and the rotation-driving feature of knee prosthesis 140 of FIGS. 27 and 28 (i.e., tibial component 144 having a concave anterior section 154 and a concave posterior section 156 separated by inflection point 158).

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A knee prosthesis that is configured to articulate between an extended position and a flexed position, the knee prosthesis comprising:
    a femoral component including a medial condyle having a medial wall and a lateral condyle having a lateral wall, wherein the medial and lateral walls come to a point and define a triangular shaped opening therebetween; and
    a tibial component including:
        a medial surface sized to receive the medial condyle of the femoral component;
        a lateral surface sized to receive the lateral condyle of the femoral component; and
        a central eminence extending proximally from the tibial component and configured to project between the medial and lateral walls, the central eminence having an anterior portion with flat surfaces forming a triangular cross-section that comes to a point and is configured to engage the triangular shaped opening and prevent relative rotation between the tibial and femoral components in the extended position.

2. The knee prosthesis of claim 1, wherein the central eminence includes:
    the anterior portion projecting between the medial and lateral walls in the extended position; and
    a posterior portion configured to project between the medial and lateral walls in the flexed position.

3. The knee prosthesis of claim 2, wherein the anterior portion of the central eminence conforms tightly to the triangular shaped opening in the extended position, and the posterior portion of the central eminence loosely fits between the medial and lateral walls in the flexed position.

4. The knee prosthesis of claim 3, wherein the posterior portion has a rounded cross-section.

5. The knee prosthesis of claim 4, wherein the central eminence gradually transitions between the triangular cross-section and the rounded cross-section.

6. The knee prosthesis of claim 3, wherein the medial and lateral walls are flat.

7. The knee prosthesis of claim 3, wherein the central eminence has a decreasing height in an anterior to posterior direction.

8. The knee prosthesis of claim 7, wherein the central eminence flattens in the anterior to posterior direction.

9. The knee prosthesis of claim 3, wherein the central eminence has a proximal end spaced from the femoral component in both the extended position and the flexed position.

10. The knee prosthesis of claim 3, wherein the knee prosthesis transitions from the extended position to the flexed position between 10° and 30° of knee flexion, wherein the extended position is more constrained than the flexed position.

11. The knee prosthesis of claim 1, wherein a radius of curvature of one or both of the medial and lateral condyles decreases in size in an anterior to posterior direction.

12. The knee prosthesis of claim 1, wherein a width of the medial and lateral condyles decreases in size in an anterior to posterior direction.

13. A knee prosthesis that articulates between an extended position and a flexed position, the extended position defined as including full extension up to 20° of knee flexion, the knee prosthesis comprising:
    a femoral component including a medial condyle having an inner medial wall and a lateral condyle having an inner lateral wall, the inner medial and lateral walls being flat to define a triangular shaped opening therebetween; and
    a tibial component including:
        a medial surface configured for contact with at least a portion of the medial condyle of the femoral component;
        a lateral surface configured for contact with at least a portion of the lateral condyle of the femoral component; and
        a central eminence extending proximally from the tibial component and projecting between the medial and lateral condyles of the femoral component in both the extended position and the flexed position, the central eminence having less contact with the inner medial and lateral walls when the knee prosthesis is in the flexed position than when the knee prosthesis is in the extended position such that the femoral and tibial components are more constrained, due to contact between the central eminence and the inner medial and lateral walls, against movement relative to each other when the knee prosthesis is in the extended position than when the knee prosthesis is in the flexed position;
    wherein the central eminence has an anterior portion including flat surfaces coming to a point and forming a triangular cross-section to engage the triangular shaped opening and prevent relative rotation between the tibial and femoral components in the extended position.

14. The knee prosthesis of claim 13, wherein a posterior portion of the central eminence has a rounded cross-section, and wherein the central eminence gradually transitions between the triangular cross-section and the rounded cross-section.

15. The knee prosthesis of claim 13, wherein the central eminence has a decreasing height in an anterior to posterior direction, and wherein the central eminence flattens in the anterior to posterior direction.

16. The knee prosthesis of claim 13, wherein the central eminence has a proximal end spaced from the femoral component in both the extended position and the flexed position.

17. The knee prosthesis of claim 13, wherein the movement of the femoral and tibial components relative to each other includes a rotational movement of the femoral component relative to the tibial component about an axis that is medially offset from a center of the knee prosthesis, and the medial and lateral condyles of the femoral component and the medial and lateral surfaces of the tibial component continue to drive rotation of the femoral component relative to the tibial component about the axis as the knee prosthesis articulates from the extended position to the flexed position.

18. The knee prosthesis of claim 13, wherein the movement of the femoral and tibial components relative to each other includes at least one of:
   an anterior movement of the tibial component relative to the femoral component; and
   a lateral movement of the femoral component relative to the tibial component; and
   whereby the knee prosthesis resists the movement to a greater extent when the knee prosthesis is in the extended position than when the knee prosthesis is in the flexed position.

19. The knee prosthesis of claim 13, wherein:
   the inner medial wall of the medial condyle and the inner lateral wall of the lateral condyle come to a point to define the triangular shaped opening.

* * * * *